United States Patent
Cost et al.

(10) Patent No.: US 10,889,834 B2
(45) Date of Patent: Jan. 12, 2021

(54) METHODS AND COMPOSITIONS FOR ENHANCING TARGETED TRANSGENE INTEGRATION

(71) Applicant: Sangamo BioSciences, Inc., Richmond, CA (US)

(72) Inventors: Gregory J. Cost, Richmond, CA (US); Thomas Wechsler, Richmond, CA (US)

(73) Assignee: Sangamo Therapeutics, Inc., Brisbane, CA (US)

(*) Notice: Subject to any disclaimer, the term of this patent is extended or adjusted under 35 U.S.C. 154(b) by 63 days.

(21) Appl. No.: 14/967,885

(22) Filed: Dec. 14, 2015

(65) Prior Publication Data

US 2016/0168593 A1 Jun. 16, 2016

Related U.S. Application Data

(60) Provisional application No. 62/092,160, filed on Dec. 15, 2014.

(51) Int. Cl.
| | | |
|---|---|---|
| *C12N 15/90* | (2006.01) | |
| *A61K 31/4745* | (2006.01) | |
| *A61K 31/7048* | (2006.01) | |
| *A61K 48/00* | (2006.01) | |

(52) U.S. Cl.
CPC ........ *C12N 15/907* (2013.01); *A61K 31/4745* (2013.01); *A61K 31/7048* (2013.01); *A61K 48/00* (2013.01); *C12N 2750/14143* (2013.01)

(58) Field of Classification Search
CPC ........ C12N 15/907; C12N 2750/14143; A61K 31/4745; A61K 31/7048; A61K 48/00
See application file for complete search history.

(56) References Cited

U.S. PATENT DOCUMENTS

| | | | |
|---|---|---|---|
| 5,356,802 A | 10/1994 | Chandrasegaran | |
| 5,436,150 A | 7/1995 | Chandrasegaran | |
| 5,487,994 A | 1/1996 | Chandrasegaran | |
| 5,789,538 A | 8/1998 | Rebar et al. | |
| 5,925,523 A | 7/1999 | Dove et al. | |
| 6,007,988 A | 12/1999 | Choo | |
| 6,013,453 A | 1/2000 | Choo | |
| 6,140,081 A | 10/2000 | Barbas | |
| 6,140,466 A | 10/2000 | Barbas, III et al. | |
| 6,200,759 B1 | 3/2001 | Dove et al. | |
| 6,242,568 B1 | 6/2001 | Barbas, III et al. | |
| 6,410,248 B1 | 6/2002 | Greisman et al. | |
| 6,453,242 B1 | 9/2002 | Eisenberg et al. | |
| 6,479,626 B1 | 11/2002 | Kim et al. | |
| 6,503,717 B2 | 1/2003 | Case et al. | |
| 6,534,261 B1 | 3/2003 | Cox, III et al. | |
| 6,599,692 B1 | 7/2003 | Case et al. | |
| 6,607,882 B1 | 8/2003 | Cox, III et al. | |
| 6,689,558 B2 | 2/2004 | Case | |
| 6,794,136 B1 | 9/2004 | Eisenberg et al. | |
| 6,824,978 B1 | 11/2004 | Cox, III et al. | |
| 6,903,185 B2 | 6/2005 | Kim et al. | |
| 6,933,113 B2 | 8/2005 | Case et al. | |
| 6,979,539 B2 | 12/2005 | Cox, III et al. | |
| 7,013,219 B2 | 3/2006 | Case et al. | |
| 7,030,215 B2 | 4/2006 | Liu et al. | |
| 7,067,317 B2 | 6/2006 | Rebar et al. | |
| 7,070,934 B2 | 7/2006 | Cox et al. | |
| 7,074,596 B2 | 7/2006 | Darzynkiewicz et al. | |
| 7,153,949 B2 | 12/2006 | Kim et al. | |
| 7,163,824 B2 | 1/2007 | Cox, III et al. | |
| 7,253,273 B2 | 8/2007 | Collingwood et al. | |
| 7,262,054 B2 | 8/2007 | Jamieson et al. | |
| 7,361,635 B2 | 4/2008 | Miller et al. | |
| 7,888,121 B2 | 2/2011 | Urnov et al. | |
| 7,914,796 B2 | 3/2011 | Miller et al. | |
| 7,951,925 B2 | 5/2011 | Ando et al. | |
| 7,972,843 B2 | 7/2011 | Hoffmann | |
| 7,972,854 B2 | 7/2011 | Miller et al. | |
| 8,034,598 B2 | 10/2011 | Miller et al. | |
| 8,110,379 B2 | 2/2012 | DeKelver et al. | |
| 8,153,773 B2 | 4/2012 | Jemielity et al. | |
| 8,409,861 B2 | 4/2013 | Guschin et al. | |
| 8,586,526 B2 | 11/2013 | Gregory et al. | |
| 8,623,618 B2 | 1/2014 | Doyon et al. | |
| 8,623,854 B2 | 1/2014 | Sullivan et al. | |
| 8,697,359 B1 | 4/2014 | Zhang | |

(Continued)

FOREIGN PATENT DOCUMENTS

| | | |
|---|---|---|
| GB | 2338237 A | 12/1999 |
| WO | WO 95/19431 A1 | 7/1995 |

(Continued)

OTHER PUBLICATIONS

Russell et al., PNAS, 92: 5719-5723, 1995.*
Russell et al., PNAS, 91: 8915-8919, 1994.*
Schultz et al., Molecular Therapy, 16(7): 1189-119, 2008.*
Hong et al., World J Gastroenterol 2004;10(8):1191-1197.*
Pommier et al., ACS Chem Biol. Jan. 18, 2013; 8(1): 82-95.*
Auilera and Gomez-Gonzalez., "Genome Instabilty: A Mechanistic View of its Causes and Consequences." *Nature Reviews Genetics* 9:204-217 (2008).
Barzel, et al., "Promoterless Gene Targeting Without Nucleases Ameliorates Haemophilia B in Mice," *Nature* 517:360-364 (2015) doi:10.1038/nature13864 (2014).
Beerli, et al., "Engineering Polydactyl Zinc-Finger Transcription Factors," *Nature Biotechnol.* 20:135-141(2002).
Beurdeley. et al., "Compact Designer Talens for Efficient Genome Engineering," *Nat. Comm.* 1-8, doi:10.1038.ncomms2782 (2013).
Boch, et al., "Breaking the Code of DNA Binding Specificity of Tal-Type III Effectors," *Science* 326:1509-1512 (2009).
Boissel, et al., "Megatals: A Rare-Cleaving Nuclease Architecture for Therapeutic Genome Engineering." *Nucleic Acids Research* 1-11(2013) doi:10.1093/nar/gkt1224.

(Continued)

Primary Examiner — Thaian N. Ton
(74) Attorney, Agent, or Firm — Pasternak Patent Law

(57) ABSTRACT

Disclosed herein are methods and compositions for enhancing insertion of transgene sequences encoding proteins that is aberrantly expressed in disease or disorder such as a lysosomal storage disease or a hemophilia by administering one or more topoisomerases inhibitors, one or more stabilizers of R loop formation or inhibitors of R-loop repair and/or one or more up-regulators of the TC-NER pathway to the target cell.

11 Claims, 1 Drawing Sheet

(56) References Cited

U.S. PATENT DOCUMENTS

| | | | |
|---|---|---|---|
| 8,703,489 | B2 | 4/2014 | Wang |
| 8,771,985 | B2 | 7/2014 | Cui et al. |
| 8,932,814 | B2 | 1/2015 | Cong et al. |
| 8,945,868 | B2 | 2/2015 | Collingwood et al. |
| 9,005,973 | B2 | 4/2015 | Cost et al. |
| 9,045,763 | B2 | 6/2015 | DeKelver et al. |
| 2003/0232410 | A1 | 12/2003 | Liljedahl et al. |
| 2005/0026157 | A1 | 2/2005 | Baltimore et al. |
| 2005/0064474 | A1 | 3/2005 | Urnov et al. |
| 2005/0208489 | A1 | 9/2005 | Carroll et al. |
| 2005/0267061 | A1 | 12/2005 | Martin |
| 2006/0063231 | A1 | 3/2006 | Li et al. |
| 2006/0188987 | A1 | 8/2006 | Guschin et al. |
| 2007/0134796 | A1* | 6/2007 | Holmes ............. A61K 48/0008 435/455 |
| 2007/0218528 | A1 | 9/2007 | Miller |
| 2008/0131962 | A1 | 6/2008 | Miller |
| 2008/0159996 | A1 | 7/2008 | Ando et al. |
| 2009/0068164 | A1 | 3/2009 | Segal et al. |
| 2009/0305346 | A1 | 12/2009 | Miller |
| 2010/0047805 | A1 | 2/2010 | Wang |
| 2010/0218264 | A1 | 8/2010 | Cui et al. |
| 2011/0207221 | A1 | 8/2011 | Cost et al. |
| 2011/0265198 | A1 | 10/2011 | Gregory et al. |
| 2011/0281361 | A1 | 11/2011 | DeKelver et al. |
| 2012/0017290 | A1 | 1/2012 | Cui et al. |
| 2012/0128635 | A1 | 5/2012 | Gregory et al. |
| 2012/0195936 | A1 | 8/2012 | Rudolph et al. |
| 2013/0122591 | A1 | 5/2013 | Cost et al. |
| 2013/0137104 | A1 | 5/2013 | Cost et al. |
| 2013/0177960 | A1 | 7/2013 | Rebar |
| 2013/0177983 | A1 | 7/2013 | Rebar |
| 2013/0183368 | A1 | 7/2013 | Hutchison et al. |
| 2014/0017212 | A1 | 1/2014 | Rebar |
| 2015/0056705 | A1 | 2/2015 | Conway et al. |
| 2015/0159172 | A1 | 6/2015 | Miller et al. |

FOREIGN PATENT DOCUMENTS

| | | |
|---|---|---|
| WO | WO 96/06166 A1 | 2/1996 |
| WO | WO 98/37186 A1 | 8/1998 |
| WO | WO 98/53057 A1 | 11/1998 |
| WO | WO 98/53058 A1 | 11/1998 |
| WO | WO 98/53059 A1 | 11/1998 |
| WO | WO 98/53060 A1 | 11/1998 |
| WO | WO 98/54311 A1 | 12/1998 |
| WO | WO 00/27878 A1 | 5/2000 |
| WO | WO 01/60970 A2 | 8/2001 |
| WO | WO 01/88197 A2 | 11/2001 |
| WO | WO 02/016536 A1 | 2/2002 |
| WO | WO 02/077227 A2 | 10/2002 |
| WO | WO 02/099084 A2 | 12/2002 |
| WO | WO 03/016496 A2 | 2/2003 |
| WO | WO 07/014275 A2 | 2/2007 |
| WO | WO 09/042163 A1 | 4/2009 |
| WO | WO 10/079430 A1 | 7/2010 |

OTHER PUBLICATIONS

Bonas, et al., "Genetic and Structural Characterization of the Avirulence Gene AVRBS3 From Xantromonas Campestris PV. Vesicatoria." Mol. Gen. Genet. 218:127-136 (1989).

Chang, et al., "Modification of DNA Ends Can Decrease End Joining Relative to Homolgous Recombination in Mammalian Cells." PNAS USA 84:4959-4963 (1987).

Choo, et al , "Advances in Zinc Finger Engineering," Curr. Opin. Struct. Biol. 10:411-416 (2000).

De Bont and van Larebeke. "Endogenous DNA Damage in Humans: A Review of Quantitative Data," Mutagenesis 19(3):169-185 (2004).

Haft, et al., "A Guild of 45 CRISPR-Associated (CAS) Protein Families and Multiple CRISPR/CAS Subtypes Exist in Prokaryotic Genomes," PloS Comput. Biol. 1(6):474-483 (2005).

Heuer, et al., "Repeat Domain Diversity of AVRBS3-Like Genes in Ralstonia Solanacearum Strains and Association With Host Preferences in the Field," Appl. And Envir. Micro. 73(13):4379-4384 (2007).

Holt, et al., "Human Hematopoietic Stem/Progenitor Cells Modified by Zinc-Finger Nucleases Targeted to CCR5 Control HIV-1 In Vivo," Nature Biotech. 28:839-847 (2010).

Isalan, et al., "A Rapid, Generally Applicable Method to Engineer Zinc Fingers Illustrated by Targeting the HIV-1 Promoter." Nat. Biotechnol. 19:656-660 (2001).

Iyama, et al., "DNA Repair Mechanisms in Dividing and Non-Dividing Cells," DNA Repair (Amst.) 12(8):620-636 (2013) doi:10.1016/j. dnarep.2013.04.015.

Jacotot, et al., "Therapeutic Peptides: Targeting the Mitochondrion to Modulate Apoptosis," Biochim. Biophys. Acta. Bioeng. 1757(9-10):1312-1323 (2006).

Jansen, et al., "Identification of Genes That are Associated With DNA Repeats in Prokaryotes," Molecular Microbiology 43(6):1565-1575 (2002).

Karkan, et al., "-A Unique Carrier for Delivery of Therapeutic Compounds Beyond the Blood-Brain Barrier," PLOS One 3(6):e2469 (2008) doi:10.1371/journal.pone.0002469s.

Kay. et al., "A Bacterial Effector Acts as a Plant Transcription Factor and Induces a Cell Size Regulator," Science 318:648-651 (2007).

Kim, et al., "Insertion and Deletion Mutants of FOK1 Restriction Endonuclease," J Biol. Chem. 269:31.978-31.978-31.982 (1994b).

Kim, et al., "Chimeric Restriction Endonuclease," PNAS USA 91:883-887 (1994a).

Kormann, et al., "Expression of Therapeufic Proteins After Delivery of Chemically Modified MRNA in Mice," Nature Biotechnology 29(2):154-157 (2011).

Kuraoka, et al., "Effects of Endogenous DNA Base Lesions on Transcription Elongation by Mammalian RNA Polymerase II" J. Biol. Chem. 283:940-950 (2008).

Kuraoka, et al., "Isolaton of XAB2 Complex Involved in Pre-MRNA Splicing, Transcription. And Transcription-Coupled Repair," The Journal of Biological Chemistry 283(2):940-950 (2008).

Li, et al., "Functional Domains in FOK 1 Restriction Endonuclease," PNAS USA 89:4275-4279 (1992).

Li, et al., "Alteration of the Cleavage Distance of FOK 1 Restriction Endonuclease by Insertion Mutagenesis," PNAS USA 90:2764-2768 (1993).

Makarova, et al., "A DNA Repair System Specific for Thermophilic Archaea and Bacteria Predicted by Genomic Context Analysis," Nucleic Acids Res. 30:482-496 (2002).

Makarova, et al., "A Putative RNA-Interference-Based Immune System in Prokaryotes: Computational Analysis of the Predicted Enzymatic Machinery, Functional Analogies With Eukaryotic RNAi, and Hypothetical Mechanisms of Action," Biol. Direct 1:7 (2006).

McIntosh, et al., "Therapeutic Levels of FVIII Following a Single Peripheral Vein Administration of RAAV Vector Encoding a Novel Human Factor VIII Variant," Blood 121(17):3335-3344(2013).

Mistrry, et al., "DNA Topoisomerase II in Therapy-Related Acute Promyelocytic Leukemia," The New England Journal of Medicine 352(15):1529-1538 (2005).

Moscou. et al., "A Simple Cipher Governs DNA Recognition by TAL Effectors." Science 326:1501 (2009).

Olovnikov, et al., "Bacterial Argonaute Samples the Transcriptome to Identify Foreign DNA," Mol. Cell. 51(5):594-605 (2013).

Pabo, et al., "Design and Selection of Novel CYS2HIS2 Zinc Finger Proteins," Ann. Rev. Biochem. 70:313-340 (2001).

Pederson, et al., "DNA Topoisomerases Maintain Promoters in a State Competent for Transcriptional Activation in Saccharomyces cerevisiae," PLOS Genetics 8(12):1 (2012).

Pommier, "Drugging Topoisomerases: Lessons and Challenges," ACS Chem. Biol. 8(1):82-95 (2013).

Ran et al., "In Vivo Genome Editing Using Staphylococcus aureus CAS9." Nature 520:186 (2015).

Schornack, et al., "Gene-For-Gene-Mediated Recognition of Nuclear-Targeted AVRBS3-Like Bacterial Effector Proteins," J. Plant Physiol. 163(3):256-272 (2006).

Segal, et al., "Custom DNA-Binding Proteins Come of Age: Polydactyl Zinc-Finger Proteins," Curr. Opin. Biotechmol 12:632-637 (2001).

(56) References Cited

OTHER PUBLICATIONS

Sheng. et al., "Structure-Based Cleavage Mechanism of Thermus Thermophilus Argonaute DNA Guide Strand-Mediated DNA Target Cleavage," *Proc. Natl. Acad. Sci. USA* 111(2):652-657 (2013) doi: 10.1073/pnas.1321032111.

Skourti-Stathaki and Proudfoot, "A Double-Edged Sword: R Loops as Threats to Genome Integrity and Powerful Regulators of Gene Expression," *Genes Dev.* 28(13):1384-1396; doi.10.1101 (2014).

Sollier, et al., "Transcription-Coupled Nucleotide Excision Repair Factors Promote R-Loop-Induced Genome Instability," *Molecular Cell* 56:777-785 (2014).

Svensson, et al., "In Vitro and In Vivo Activities of a Doxorubicin Prodrug in Combination With Monoclonal Antibody Beta-Lactamase Conjugates," *Cancer Research* 55(11):2357-2365 (1995).

Swarts, et al., "DNA-Guided DNA Interference by a Prokaryotic Argonaute" *Nature* 507(7491):258-261 (2014).

Teves and Henikoff, "DNA Torsion as a Feedback Mediator of Transcription and Chromatin Dynamics," *Nucleus* 5(3):211-218 (2014).

Vogel, et al., "A Bacterial Seek-and-Destroy System for Foreign DNA" *Science* 344:972-973 (2014).

Yuan, et al., Crystal Structure of A. Aeolicus Argonaute. A Site-Specific DNA-Guided Endoribonuclease, Provides Insights Into Risc-Mediated MRNA Cleavage, *Molecular Cellular* 19:405-419 (2005).

\* cited by examiner

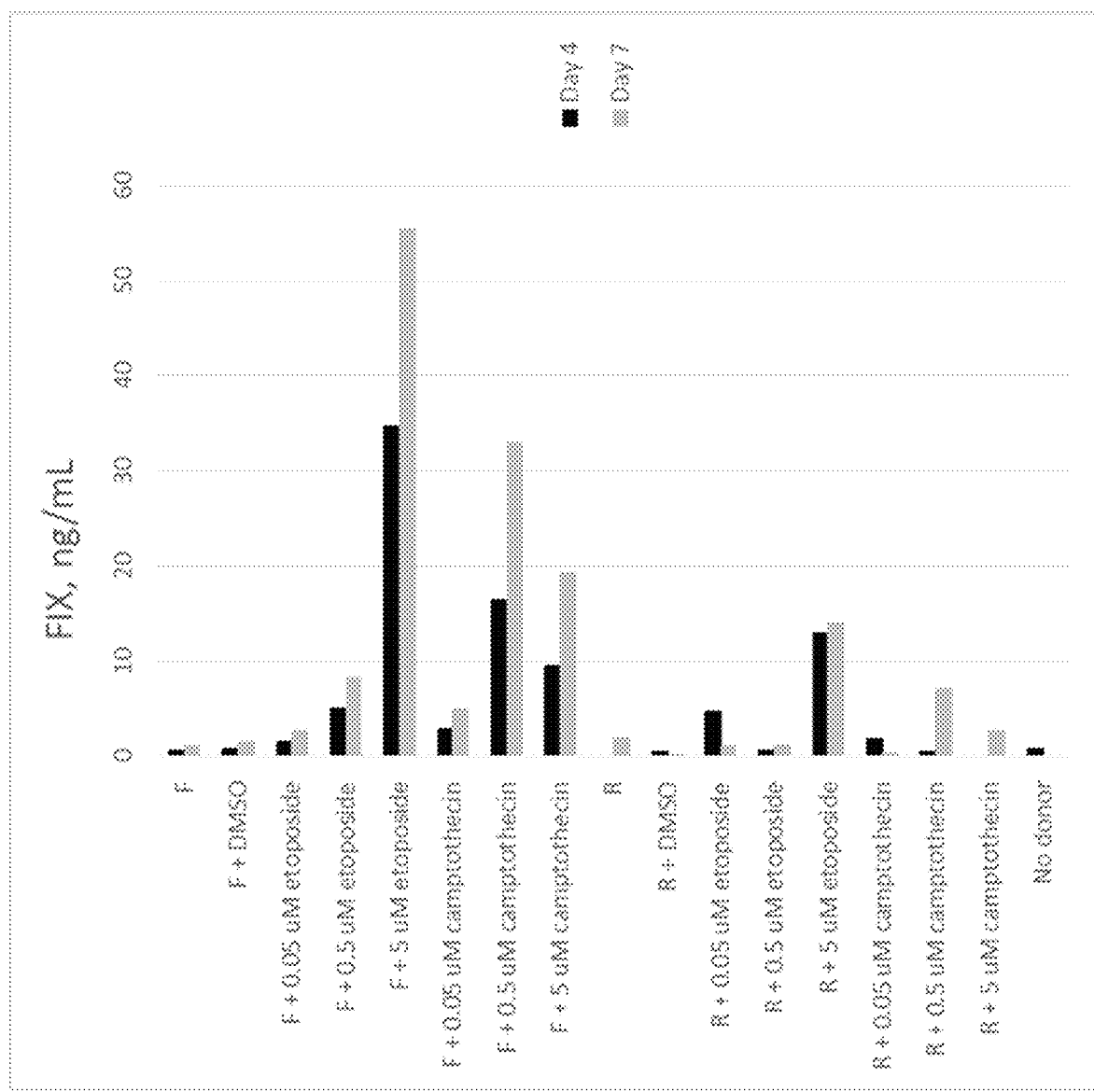

METHODS AND COMPOSITIONS FOR ENHANCING TARGETED TRANSGENE INTEGRATION

CROSS-REFERENCE TO RELATED APPLICATIONS

The present application claims the benefit of U.S. Provisional Application No. 62/092,160, filed Dec. 15, 2014, the disclosure of which is hereby incorporated by reference in its entirety.

STATEMENT OF RIGHTS TO INVENTIONS MADE UNDER FEDERALLY SPONSORED RESEARCH

Not applicable.

TECHNICAL FIELD

The present disclosure is in the fields of gene modification, particularly targeted integration of a gene.

BACKGROUND

Gene therapy holds enormous potential for a new era of human therapeutics. These methodologies will allow treatment for conditions that heretofore have not been addressable by standard medical practice. One area that is especially promising is the ability to add a transgene to a cell to cause that cell to express a product that previously not being produced in that cell. Examples of uses of this technology include the insertion of a gene encoding a therapeutic protein, insertion of a coding sequence encoding a protein that is somehow lacking in the cell or in the individual and insertion of a sequence that encodes a structural nucleic acid such as a microRNA.

Transgenes can be delivered to a cell by a variety of ways, such that the transgene becomes integrated into the cell's own genome and is maintained there. In recent years, a strategy for transgene integration has been developed that uses cleavage with site-specific nucleases for targeted insertion into a chosen genomic locus (see, e.g., U.S. Pat. No. 7,888,121). Nucleases, such as zinc finger nucleases (ZFNs), transcription activator-like effector nucleases (TALENs), or nuclease systems such as the CRISPR/Cas system (utilizing an engineered guide RNA) or a TtAgo system, are specific for targeted genes and can be utilized such that the transgene construct is inserted by either homology directed repair (HDR) or by end capture during non-homologous end joining (NHEJ) driven processes.

Any locus may be targeted, including "safe harbor" loci such as the AAVS1, HPRT, albumin and CCR5 genes. See, e.g., U.S. Pat. Nos. 9,045,763; 9,005,973; 8,956,828; 8,945,868; 8,586,526; 6,534,261; 6,599,692; 6,503,717; 6,689,558; 7,067,317; 7,262,054; 7,888,121; 7,972,854; 7,914,796; 7,951,925; 8,110,379; 8,409,861; U.S. Patent Publications 20030232410; 20050208489; 20050026157; 20050064474; 20060063231; 20080159996; 201000218264; 20120017290; 20110265198; 20130137104; 20130122591; 20130177983 and 20130177960 and 20150056705. Nuclease-mediated integration offers the prospect of improved transgene expression, increased safety and expressional durability, as compared to classic integration approaches that rely on random integration of the transgene, since it allows exact transgene positioning for a minimal risk of gene silencing or activation of nearby oncogenes.

In some instances, it has been found that delivery of a transgene alone is sufficient to cause integration of that exogenous DNA into the genome of a cell. (see Barzel et al (2014) Nature doi: 10.1038/nature13864). Nicks and double-strand breaks occur naturally in the DNA of a cell due to many factors such as the presence of reactive oxygen species as a result of metabolic processes and exposure to ultraviolet light (see De Bont and van Larebeke, (2004) Mutagenesis 19(3):169). Introduced exogenous DNA can be captured in such DNA nicks and breaks through mechanisms such as nonhomologous end joining (NHEJ)-mediated capture or homology dependent recombination (HDR).

Another way that nicks and double-strand DNA breaks can occur can be as a result of failure of topoisomerases to complete their reaction cycle, either spontaneously or due to exposure to compounds known as topoisomerase poisons. During DNA replication and transcription, the opening of the two DNA strands generates torsional tension and supercoiling on both ends of the opening. Positive supercoiling ahead of polymerases causes the DNA helix to tighten while negative supercoiling behind polymerases can facilitate the formation of abnormal structures in the DNA such as, z-DNAs. Topoisomerases act to relieve this added tension by causing breaks, either nicks or double-strand breaks, in the DNA backbone which allow the DNA to untwist in a controlled manner (Teves and Henikoff (2014) *Nucleus* 5(3):211). In addition, it has been shown that genes that are more highly expressed are more dependent upon the presence of topoisomerase activity (Pederson et al (2012) *PLOS Genetics* 8(12):1). The topoisomerase breaks the DNA through a transesterification reaction where an active site tyrosine in the topoisomerase attacks the phosphodiester backbone of the DNA helix. Small molecules can act as topoisomerase poisons by inhibiting their activity, often trapping the DNA:topoisomerase complex in a vulnerable stage (e.g. Top2cc or Top1cc) after the DNA has been broken but prior to its re-ligation, such that breaks may occur (see Pommier (2013) *ACS Chem Biol* 8(1): 82-95). Best known of this class of molecules are number of drugs used in chemotherapeutic oncology treatment such as anthracyclines (e.g. doxorubicin) and camptothecins. These molecules are very specific and have the ability to target type I topoisomerases (nickases) or type II topoisomerases exclusively (double strand cleavage). These compounds often intercalate into the DNA double strand and interact simultaneously with the DNA and the topoisomerase enzyme to stabilize the complex, leading to an increase in double strand breaks in the DNA near topoisomerases.

An alternative mechanism by which spontaneous DSB can occur is transcription-associated genomic instability. Here the breakage of the DNA is not carried out by a topoisomerase but by nucleolytic activities of the DNA repair enzymes encoded by the genes like XPF/XPG or yet to be identified proteins. As mentioned above, as the transcription machinery progresses across a gene, following in its path is a region of negative supercoil which can lead to the formation of R loops. These are single stranded DNA structures that can form when the mRNA being generated by the RNA polymerase complex forms a RNA-DNA hybrid structure in the still-opened DNA helix on the transcribed strand, creating the R loop from the untranscribed single stranded DNA. This happens more often if RNA-Polymerase II (RNA-PII) complexes are stalled, which can occur at both the 5' and 3' ends of highly-transcribed genes.

R-loops are also formed during cleavage by a CRISPR/Cas9 complex (Skourti-Stathaki and Proudfoot (2014) *Genes Dev* 28(13):1384-1396, doi/10.1101)

These R loop structures caused by RNA-DNA hybrids are associated with such processes as AID-mediated class switching in Ig genes in B cells (see Auilera and Gomez-Gonzalez (2008) *Nature Reviews Genetics* 9:204). If these R loops are not dissociated by either RNAase H1 (or occasionally, RNAase-H2) or DNA:RNA helicases they are associated with DNA damage accumulation and genome instability, which may be associated with transcription-coupled nucleotide excision repair (TC-NER). Factors that are part of TC-NER include the Aquarius (AQR) protein which has putative RNA-DNA helicase activity and could help to resolve R-loops. Recently it has been shown that knock down of AQR in human cells leads to DSB formation (see Sollier et al (2014) *Molecular Cell* 56:1-9). Additionally, there are two nucleases that act on open DNA structures in nucleotide excision repair pathways to repair bulky DNA lesions in the genome cause by a number of DNA damaging agents. These nucleases (XPT and XPG) appear to act on R loops that appear from AQR knockdown, creating stretches of ss-DNA, leading to genomic instability and double strand breaks.

Thus, there remains a need for additional methods and compositions that can be used to increase the frequency of integration of transgenes into a cell.

SUMMARY

Disclosed herein are methods and compositions that can be used to enhance integration and/or expression of a transgene integrated into a genome. In some embodiments, the transgene is integrated into an endogenous gene, for example an albumin gene and expression of the transgene is controlled by the endogenous albumin promoter. Integration may be mediated (facilitated) by one or more nucleases or may be achieved in the absence of any nucleases. In some aspects, the transgene may encode a therapeutic protein of interest. The transgene may encode a protein such that the methods of the invention can be used for production of protein that is deficient or lacking (e.g., "protein replacement"). In some instances, the protein may be involved treatment for a lysosomal storage disease. Other therapeutic proteins may be expressed, including protein therapeutics for conditions as diverse as epidermolysis bullosa, diabetes, cancer, clotting disorders or AAT deficient emphysema. In other aspects, the transgene may comprise sequences (e.g., engineered sequences) such that the expressed protein has characteristics which give it novel and desirable features (increased half-life, changed plasma clearance characteristics etc.). Engineered sequences can also include amino acids derived from the albumin sequence. In some aspects, the transgenes encode therapeutic proteins, therapeutic hormones, plasma proteins, antibodies and the like. In some aspects, the transgenes may encode proteins involved in blood disorders such as clotting disorders. In some aspects, the transgenes encode structural nucleic acids (shRNAs, RNAi, miRNAs and the like). The donor molecule (e.g., vector) carrying the transgene may include homology arms flanking the transgene, including homology arms to a selected endogenous gene.

In one aspect, described herein is a method of increasing the frequency of transgene integration into a cell. In one embodiment, the methods of the invention are performed without the use of targeted engineered nucleases (e.g., ZFNs, TALENs, CRIPSR/Cas or TtaGo systems). The methods include introducing one or more transgenes into a cell and growing the cell in the presence of topoisomerase inhibitors, one or more stabilizers of R loop formation or inhibitors of R-loop repair and/or one or more up-regulators of the TC-NER pathway such that the transgene is integrated in the genome of the cell. In other embodiments, the methods of the invention are performed with the use of one or more engineered nucleases. The transgenes may be in mRNA form or may be carried on viral (AAV, adeno, etc.) vectors or non-viral (plasmid) vectors and may include homology arms (to the targeted region) flanking the transgene.

In another aspect, disclosed here are methods of enhancing targeted integration of a sequence into an endogenous locus of a genome, the methods comprising introducing into a cell, one or more nucleases, one or more donor sequences (transgenes) and exposing the cell (e.g., in the surrounding media) to one or more topoisomerase inhibitors. In certain embodiments, the frequency of gene targeting (integration) of the donor (transgene) sequence integration is increased.

In another aspect, one method of the invention to increase transgene integration contemplates the use of small molecule inhibitors of topoisomerase I and/or II to increase the frequency of DSB formation, for example by growing the cell comprising the transgene in the presence of one or more of the small molecule inhibitors. In some embodiments, the inhibitor may be camptothecin (a type I topoisomerase inhibitor) and/or etoposide (a type II topoisomerase inhibitor). Also contemplated are doxorubicin, cisplatin, topotecan, irinotecan, tenipopside, mitoxantrone, etoposide phosphate, and topotecan hydrochloride as well as other topoisomerase I or II inhibitors known in the art. In other embodiments, the methods contemplates one or more stabilizers of R loop formation or inhibitors of R-loop repair and/or one or more up-regulators of the TC-NER pathway to increase transgene integration. The one or more topoisomerase inhibitors, one or more stabilizers of R loop formation or inhibitors of R-loop repair and/or one or more up-regulators of the TC-NER pathway may be small molecules, peptides or polynucleotides.

The topoisomerase inhibitor(s) used in the methods and compositions for transgene integration described herein can be used at any concentration that inhibits topoisomerase activity. In certain embodiments, the concentration(s) do not cause significant genotoxicity to the target cell, for example below the concentrations (doses) used for chemotherapies. Thus, the dose of topoisomerase inhibitor may be the lowest dose used for other therapies, for example for chemotherapy, or may be 10-1000 fold (or any number therebetween) lower than the dose used for other therapies. Similarly, the one or more stabilizers of R loop formation or inhibitors of R-loop repair and/or one or more up-regulators of the TC-NER pathway may be used at any suitable concentration.

In any of the methods described herein, the transgene(s) can be integrated with or without the use of one or more nucleases. Nucleases, for example engineered meganucleases, zinc finger nucleases (ZFNs), TALE-nucleases (TALENs including fusions of TALE effectors domains with nuclease domains from restriction endonucleases and/or from meganucleases (such as mega TALEs and compact TALENs)), Ttago system and/or CRISPR/Cas nuclease systems are used to cleave DNA at a 'safe harbor' gene locus (e.g. CCR5, AAVS1, HPRT, Rosa or albumin) in the cell into which the gene is inserted. Targeted insertion of a donor transgene may be via homology directed repair (HDR) or non-homology repair mechanisms (e.g., NHEJ donor capture). The nuclease can induce a double-stranded (DSB) or single-stranded break (nick) in the target DNA. In some embodiments, two nickases are used to create a DSB by introducing two nicks. In some cases, the nickase is a ZFN, while in others, the nickase is a TALEN or a CRISPR/Cas nickase.

The optional nucleases (e.g., ZFN, CRISPR/Cas system, Ttago and/or TALEN) employed in the methods as described herein may bind to and/or cleave the region of interest in a coding or non-coding region within or adjacent to the gene, such as, for example, a leader sequence, trailer sequence or intron, or within a non-transcribed region, either upstream or downstream of the coding region. In certain embodiments, the nuclease (e.g., ZFN) binds to and/or cleaves an albumin gene. See, e.g., U.S. Publication Nos. 20130177983, 20130177960 20150056705 and 20150159172. The nuclease (e.g., ZFNs, CRISPR/Cas systems, Ttago and/or TALENs) may be provided as a polynucleotide and/or protein. The polynucleotide may be, for example, mRNA. In some aspects, the mRNA may be chemically modified (See e.g. Kormann et al, (2011) *Nature Biotechnology* 29(2):154-157). The polynucleotides may be provided within an expression vector comprising a polynucleotide, encoding one or more nucleases (e.g., ZFNs, CRISPR/Cas systems, Ttago and/or TALENs) as described herein, operably linked to a promoter. In one embodiment, the expression vector is a viral vector. In one aspect, the viral vector exhibits tissue specific tropism.

In another aspect, pharmaceutical compositions comprising one or more topoisomerase inhibitors, one or more stabilizers of R loop formation or inhibitors of R-loop repair and/or one or more up-regulators of the TC-NER pathway and, optionally, one or more nucleases (and/or polynucleotides encoding the nucleases) are provided. In some embodiments, the pharmaceutical composition may comprise more than one expression vector. The pharmaceutical composition may further comprise a donor sequence (e.g., a transgene encoding a protein lacking or deficient in a disease or disorder such as an LSD or a hemophilia). In some embodiments, the donor sequence is associated with an expression vector.

In a further aspect, one method of the invention to increase transgene integration contemplates the use of compounds that stabilize R loops, including but not limited to compounds that inhibit the activity or knock down enzyme components of complexes suppressing the formation or persistence of R loops. Examples of these enzymes include the well characterized RNAases H1/H2 but also AQR, Sentataxin and other related potential RNA:DNA helicases (some with DEAxQ motif). Further this includes regulatory factors of these enzymes, e.g. the complex partners of AQR, which are XAB2, PRP19, CCDC16, PPIE and hISY1 (Kuraoke et al. (2008) *J. Biol Chem* 283:940-950) and XPG. Methods of knock down that may be used include specific small molecule inhibitors that act on the enzymes as well as knock down of expression of these proteins through such tools as specific transcription repression and RNAi inhibition. In some embodiments, these inhibitors are used without the presence of an engineered nuclease and cause an increase in integration of a donor nucleic acid in a target cell. In other embodiments, the inhibitors are use with an engineered nuclease (e.g. a ZFN, TALEN, CRISPR/Cas or Ttago system). Particularly useful is a method to increase the activity of a CRISPR/Cas system by use of an inhibitor that increases the stabilization of R loops.

In certain aspect, in order to maximize DSB generation and transgene integration, these factors in the NER pathway (by compounds that up-regulate the TC-NER pathway) are used as targets for methods to: a) upregulate their expression, b) increase their stability in the cell (e.g. ubiquitination mutants) and/or c) modulate regulatory proteins which affect their activity by post-translational modifications (e.g. kinases/phosphatases etc.) which in turn increases targeted transgene integration.

In one aspect, the methods and compositions of the invention comprise genetically modified cells comprising a transgene expressing a functional version of a protein that is aberrantly expressed in a hemophilia (Factor VII, F8, F.IX and/or Factor X protein), in which the transgene is integrated at increased levels into an endogenous safe-harbor gene (e.g., albumin gene) of the cell's genome using one or more topoisomerase inhibitors, R-loops stabilizers and/or compounds to increase members of the TC-NER pathway. In another aspect, the methods and compositions of the invention comprise genetically modified cells comprising a transgene expressing a functional version of a protein that is lacking or abnormally expressed in a subject with a lysosomal storage disease. In some embodiments, the transgene is integrated without using a nuclease. In certain other embodiments, the transgene is integrated in a site-specific (targeted) manner using at least one nuclease. In certain embodiments, the nuclease (e.g., ZFNs, TALENs, Ttago and/or CRISPR/Cas systems) is specific for a safe harbor gene (e.g. CCR5, HPRT, AAVS1, Rosa or albumin). See, e.g., U.S. Pat. Nos. 7,951,925 and 8,110,379; U.S. Publication Nos. 20080159996; 201000218264; 20120017290; 20110265198; 20130137104; 20130122591; 20130177983; 20130177960; 20150056705 and 20150159172). In some embodiments, the safe harbor is an albumin gene.

In another aspect, described herein is a method of genetically modifying a cell, in vitro and/or in vivo, to produce a therapeutic protein (e.g., a protein lacking in a disease or disorder such as a hemophilia (Factor VII, F8, F.IX and/or Factor X) or a lysosomal storage disease (IDS, IDUA, etc.), the method comprising delivering a suitable transgene donor in the presence of one or more topoisomerase inhibitors, R-loops stabilizers and/or modulators of the TC-NER pathway, optionally cleaving an endogenous safe harbor gene in the cell using one or more nucleases (e.g., ZFNs, TALENs, CRISPR/Cas), such that a transgene encoding the therapeutic protein is integrated into the safe harbor locus and/or expressed in the cell at increased frequency or levels as compared to untreated cells. In certain embodiments, the safe harbor gene is a CCR5, HPRT, AAVS1, Rosa or albumin gene. In a further aspect, described herein is a method of genetically modifying a cell, in vitro and/or in vivo, to produce a protein that is lacking in a lysosomal storage disease. The most common examples of these are glucocerebrosidase deficiency (gene name: GBA), associated with Gaucher's disease, a galactosidase deficiency (gene name: GLA), associated with Fabry's disease, iduronate-2-sulfatase deficiency (gene name: IDS), associated with Hunter's disease, alpha-L iduronidase deficiency (gene name: IDUA), associated with Hurler's disease, and sphingomyelin phosphodiesterase 1deficiency (gene name: SMPD1), associated with Niemann-Pick's disease. In certain embodiments, the cell is a mammalian cell. In certain embodiments, the cell is a primate cell. In certain embodiments, the cell is a human cell. In one set of embodiments, method are provided for inserting a transgene into an albumin gene. In another set of embodiments, methods for cleaving an albumin gene in a cell (e.g., a liver cell) are provided comprising introducing, into the cell, one or more expression vectors disclosed herein under conditions such that the one or more proteins are expressed and the albumin gene is cleaved. The albumin gene may be modified, for example, by integration of a donor sequence into the cleaved albumin gene. In other embodiments, the albumin gene may be modified by integration of a donor sequence comprising homology arms. Integration of the donor sequence into the albumin gene may be accomplished with or without the use of an engineered nuclease. In certain embodiments, the method comprises genetically modifying a cell to produce a clotting factor or a protein lacking in a lysosomal storage disease, the method comprising administering to the cell one or more nucleases, one or more donors encoding the therapeutic protein and one or more topoisomerase inhibitors. The nucleases (e.g., ZFNs) and donor may be on the same or different vectors in any combination, for example on 3 separate vectors (e.g., AAV vectors) each carrying one of the components; one vector carrying two of the components and a separate vector carrying the 3$^{rd}$ component; or one vector carrying all 3 components.

In other aspects, the invention comprises delivery of a donor nucleic acid to a target cell. The donor may be delivered prior to, after, or along with the nucleic acid encoding the nuclease(s) and may be delivered prior to, after or along with the topoisomerase inhibitor(s). The donor nucleic acid may comprise an exogenous sequence (transgene) to be integrated into the genome of the cell, for example, an endogenous locus. In some embodiments, the donor may comprise a full length gene or fragment thereof flanked by regions of homology with the targeted cleavage site. In some embodiments, the donor lacks homologous regions and is integrated into a target locus through homology independent mechanism (i.e. NHEJ). The donor may comprise any nucleic acid sequence, for example a nucleic acid that, when used as a substrate for homology-directed repair of the nuclease-induced double-strand break, leads to a donor-specified deletion to be generated at the endogenous chromosomal locus or, alternatively (or in addition to), novel allelic forms of (e.g., point mutations that ablate a transcription factor binding site) the endogenous locus to be created. In some aspects, the donor nucleic acid is an oligonucleotide wherein integration leads to a gene correction event, or a targeted deletion. In some aspects the donor comprises a therapeutic protein, for example a clotting factor.

In some embodiments, the polynucleotide encoding the DNA binding protein is a mRNA. In some aspects, the mRNA may be chemically modified (See e.g. Kormann et al, (2011) *Nature Biotechnology* 29(2):154-157). In other aspects, the mRNA may comprise an ARCA cap (see U.S. Pat. Nos. 7,074,596 and 8,153,773). In further embodiments, the mRNA may comprise a mixture of unmodified and modified nucleotides (see U.S. Patent Publication 2012-0195936).

In another aspect, provided herein are methods for providing one or more functional proteins lacking or deficient in a mammal, or in a primate, such as a human primate, such as a human patient with an LSD and/or a hemophilia, for example for treating the disease by supplying the protein(s) lacking or deficient in the subject. In another aspect, provided herein are methods for providing a functional protein for treating a disorder in which the protein is lacking, deficient or aberrantly expressed. In certain embodiments, the methods comprise using nucleases and topoisomerase inhibitor(s), R loop stabilizer(s), inhibitor(s) of R-loop repair and/or up-regulator(s) of the TC-NER pathway to integrate a sequence encoding the functional protein or structural polynucleotide in a cell in a subject in need thereof. In other embodiments, the method comprises administering a genetically modified cell (expressing a functional version of a protein that is aberrantly expressed in a subject) to the subject. Thus, an isolated cell may be introduced into the subject (ex vivo cell therapy) or a cell may be modified when it is part of the subject (in vivo). Also provided is the use of the donors, nucleases and topoisomerase inhibitors described herein for the treatment of a hemophilia (e.g., hemophilia A with Factor VIII donor, hemophilia B with Factor IX donor, Factor VII deficiency with Factor VII, Factor X deficiency with Factor X, Gaucher's with a GBA donor, Fabry's with a GLA donor, Hunter's with a IDS donor, Hurler's with a IDUA donor, and/or Niemann-Pick's with a SMPD1 donor), for example, in the preparation of medicament for treatment of a disease. In any of the compositions and methods described, the nuclease(s) and/or transgene(s) may be carried on an AAV vector, including but not limited to AAV1, AAV3, AAV4, AAV5, AAV6, AAV8, AAV9 and AAVrh10 or pseudotyped AAV such as AAV2/8, AAV8.2, AAV2/5 and AAV2/6 and the like. In certain embodiments, the nucleases and transgene donors are delivered using the same AAV vector types. In other embodiments, the nucleases and transgene donors are delivered using different AAV vector types. The nucleases and transgenes may be delivered using one or more vectors. In certain embodiments, the nucleases and/or transgene donors are delivered via intravenous (e.g., intra-portal vein) administration into the liver of an intact animal.

In any of the compositions and methods described herein, the protein encoded by the transgene may comprise a F8 protein, for example a B-Domain Deleted Factor VIII (BDD-F8). In other embodiments, the protein encoded by the transgene comprises a F.IX protein. In other embodiments, the protein encoded by the transgene comprises a Factor VII protein. In other embodiments, the protein encoded by the transgene comprises a Factor X protein. In some embodiments, the protein encoded by the transgene comprises a glucocerebrosidase. In other embodiments, the protein encoded by the transgene comprises an α galactosidase. In further embodiments, the protein encoded by the transgene comprises an iduronate-2-sulfatase. In some embodiments, the protein encoded by the transgene comprises an alpha-L iduronidase. In further embodiments, the protein encoded by the transgene comprises sphingomyelin phosphodiesterase. In any of the compositions or methods described herein, the transgene also comprises a transcriptional regulator while in others, it does not and transcription is regulated by an endogenous regulator. In another aspect, the methods of the invention comprise a composition for therapeutic treatment of a subject in need thereof. In some embodiments, the composition comprises engineered stem cells comprising a safe harbor specific nuclease, and a transgene donor encoding Factor VII, F8, F.IX, Factor X, GBA, GLA, IDS, IDUA and/or SMPD1 protein or a functional fragment and/or truncation thereof. In other embodiments, the composition comprises engineered stem cells that have been modified and express a transgene donor encoding Factor VII, F8, F.IX, Factor X, GBA, GLA, IDS, IDUA and/or SMPD1 protein or a functional fragment and/or truncation thereof.

In any of the compositions or methods described herein, the cell may be a eukaryotic cell. Non-limiting examples of suitable cells include eukaryotic cells or cell lines such as secretory cells (e.g., liver cells, mucosal cells, salivary gland cells, pituitary cells, etc.), blood cells (red blood cells), red blood precursory cells, hepatic cells, muscle cells, stem cells (e.g., embryonic stem cells, induced pluripotent stem cells, hepatic stem cells, hematopoietic stem cells (e.g., CD34+)) or endothelial cells (e.g., vascular, glomerular, and tubular endothelial cells). Thus, the target cells may be primate cells, for example human cells, or the target cells may be mammalian cells, (including veterinary animals), for example especially nonhuman primates and mammals of the orders Rodenta (mice, rats, hamsters), Lagomorpha (rabbits), Carnivora (cats, dogs), and Arteriodactyla (cows, pigs, sheep, goats, horses). In some aspects, the target cells comprise a tissue (e.g. liver). In some aspects, the target cell is a stem cell (e.g., an embryonic stem cell, an induced pluripotent stem cell, a hepatic stem cell, etc.) or animal embryo by any of the methods described herein, and then the embryo is implanted such that a live animal is born. The animal is then raised to sexual maturity and allowed to produce offspring wherein at least some of the offspring comprise the genomic modification. The cell can also comprise an embryo cell, for example, of a mouse, rat, rabbit or other mammal cell embryo. The cell may be from any organism, for example human, non-human primate, mouse, rat, rabbit, cat, dog or other mammalian cells. The cell may be isolated or may be part of an organism (e.g., subject).

In any of the methods or compositions described herein, the cell containing the engineered locus (e.g., safe harbor locus such as an albumin locus) can be a stem cell that may be useful for therapeutic purposes. Specific stem cell types that may be used with the methods and compositions of the invention include embryonic stem cells (ESC), induced pluripotent stem cells (iPSC) and hepatic or liver stem cells. The iPSCs can be derived from patient samples and from normal controls wherein the patient derived iPSC can be mutated to normal gene sequence at the gene of interest, or normal cells can be altered to the known disease allele at the gene of interest. Similarly, the hepatic stem cells can be isolated from a patient. These cells are then engineered to express the transgene of interest, expanded and then reintroduced into the patient.

In any of the methods and compositions described herein, the transgene may be integrated into the endogenous safe harbor gene such that some, all or none of the endogenous gene is expressed, for example a fusion protein with the integrated transgene. In some embodiments, the endogenous safe harbor gene is an albumin gene and the endogenous sequences are albumin sequences. The endogenous may be present on the amino (N)-terminal portion of the exogenous protein and/or on the carboxy (C)-terminal portion of the exogenous protein. The albumin sequences may include full-length wild-type or mutant albumin sequences or, alternatively, may include partial albumin amino acid sequences. In certain embodiments, the albumin sequences (full-length or partial) serve to increase the serum half-life of the polypeptide expressed by the transgene to which it is fused and/or as a carrier. In other embodiments, the transgene comprises albumin sequences and is targeted for insertion into another safe harbor within a genome. Furthermore, the transgene may include an exogenous promoter (e.g., constitutive or inducible promoter) that drives its expression or its expression may be driven by endogenous control sequences (e.g., endogenous albumin promoter). In some embodiments, the donor includes additional modifications, including but not limited to codon optimization, addition of glycosylation sites and the like.

In any of the compositions or methods described herein, transgene integration can occur without the use of an engineered nuclease. The invention contemplates the use of compounds designed to inhibit topoisomerases in vulnerable complexes such that an increase in DNA nicks and double strand breaks may occur. In addition, contemplated herein is the use of methods and compounds designed to stabilize R-loops, or to reduce or inhibit R-loop repair, such that an increase in DNA nicks and double strand breaks may occur.

In any of the compositions or methods described herein, cleavage can occur through the use of specific nucleases such as engineered zinc finger nucleases (ZFN), transcription-activator like effector nucleases (TALENs), or using the Ttago or CRISPR/Cas system with an engineered crRNA/tracr RNA ('single guide RNA') to guide specific cleavage. In some embodiments, two nickases are used to create a DSB by introducing two nicks. In some cases, the nickase is a ZFN, while in others; the nickase is a TALEN or a CRISPR/Cas system. Targeted integration may occur via homology directed repair mechanisms (HDR) and/or via non-homology repair mechanisms (e.g., NHEJ donor capture). The nucleases as described herein may bind to and/or cleave the region of interest in a coding or non-coding region within or adjacent to the gene, such as, for example, a leader sequence, trailer sequence or intron, or within a non-transcribed region, either upstream or downstream of the coding region. In certain embodiments, the nuclease cleaves the target sequence at or near the binding. Cleavage can result in modification of the gene, for example, via insertions, deletions or combinations thereof. In certain embodiments, the modification is at or near the nuclease(s) binding and/or cleavage site(s), for example, within 1-300 (or any value therebetween) base pairs upstream or downstream of the site(s) of cleavage, more preferably within 1-100 base pairs (or any value therebetween) of either side of the binding and/or cleavage site(s), even more preferably within 1 to 50 base pairs (or any value therebetween) on either side of the binding and/or cleavage site(s).

The methods and compositions described may be used to treat or prevent a disease in a subject in need thereof. In some embodiments, the compositions comprise vectors and are used to target liver cells. In other embodiments, the compositions comprise engineered stem cells and are given to a patient as a bone marrow transplant. In some instances, patients are partially or completely immunoablated prior to transplantation. In other instances, patients are treated with one or more immunosuppressive agents before, during and/or after nuclease-mediated modification an endogenous gene (e.g., targeted integration of a transgene into an albumin locus). Furthermore, any of the methods described herein may further comprise additional steps, including partial hepatectomy or treatment with secondary agents that enhance transduction and/or induce hepatic cells to undergo cell cycling. Examples of secondary agents include gamma irradiation, UV irradiation, tritiated nucleotides such as thymidine, cis-platinum, etoposide, hydroxyurea, aphidicolin, prednisolone, carbon tetrachloride and/or adenovirus.

The methods described herein can be practiced in vitro, ex vivo or in vivo. In certain embodiments, the compositions are introduced into a live, intact mammal. The mammal may be at any stage of development at the time of delivery, e.g., embryonic, fetal, neonatal, infantile, juvenile or adult. Additionally, targeted cells may be healthy or diseased. In certain embodiments, one or more of the compositions are delivered intravenously (e.g., to the liver via the intraportal vein, for example tail vein injection), intra-arterially, intraperitoneally, intramuscularly, into liver parenchyma (e.g., via injection), into the hepatic artery (e.g., via injection), and/or through the biliary tree (e.g., via injection).

For targeting the compositions to a particular type of cell, e.g., platelets, fibroblasts, hepatocytes, etc., one or more of the administered compositions may be associated with a homing agent that binds specifically to a surface receptor of the cell. For example, the vector may be conjugated to a ligand (e.g., galactose) for which certain hepatic system cells have receptors. The conjugation may be covalent, e.g., a crosslinking agent such as glutaraldehyde, or noncovalent, e.g., the binding of an avidinated ligand to a biotinylated vector. Another form of covalent conjugation is provided by engineering the AAV helper plasmid used to prepare the vector stock so that one or more of the encoded coat proteins is a hybrid of a native AAV coat protein and a peptide or protein ligand, such that the ligand is exposed on the surface of the viral particle.

A kit, comprising the compositions (e.g., genetically modified cells, transgene donors topoisomerase inhibitor(s), R-loop stabilizers and/or inhibitors of R-loop repair, and optionally ZFPs, CRISPR/Cas system and/or TALENs,) of the invention, is also provided. The kit may comprise the topoisomerase inhibitors, R-loops stabilizers, and/or inhibitors of R-loop repair, nucleic acids encoding the nucleases, (e.g. RNA molecules or nuclease-encoding genes contained in a suitable expression vector), donor molecules, suitable host cell lines, instructions for performing the methods of the invention, and the like.

These and other aspects will be readily apparent to the skilled artisan in light of disclosure as a whole.

BRIEF DESCRIPTION OF THE DRAWING

FIG. 1 is a graph showing the effect of treatment of cells with a topoisomerase inhibitor on the expression of an integrated transgene. AAV comprising a human FIX transgene were produced wherein the transgene was flanked by homology arms homologous to a region in the mouse albumin gene. Hepa1-6 cells were treated with the AAV and topoisomerase inhibitor, either etoposide or camptothecin. The FIX transgene was inserted between the homology arms either in a forward (F) orientation or a reverse (R) orientation where forward means that the reading frame of the transgene (5'→3') is in the same orientation as the reading frame at the site of integration. FIX protein was measured at days 4 and 7. A large, topoisomerase inhibitor dose-dependent increase in FIX protein was observed with the forward-orientation AAV donor but generally not with the reverse-orientation donor. Therefore, pre-treatment of the cells with topoisomerase inhibitors increased FIX production by increasing the amount of transgene integration into the Albumin locus.

DETAILED DESCRIPTION

Disclosed herein are compositions and methods for genomic modification of a cell to integrate a transgene into a cell, for instance to produce one or more therapeutic proteins whose expression or gene sequence, is aberrantly expressed in a subject and is associated with a disease or disorder, for example, a hemophilia or a lysosomal storage disease (LSD). In particular, targeted integration of the donor (transgene) is increased by administering one or more topoisomerase inhibitors, R-loop stabilizers, inhibitors of R-loop repair and/or up-regulators of the TC-NER pathway to the cell such that targeted integration frequency is increased as compared to cells not receiving these compounds. In some embodiments, the transgene is inserted into an endogenous safe harbor gene, for example, an albumin gene. The transgene can encode any protein or peptide, including proteins lacking or aberrantly expressed in a subject with a disease or disorder, for example, a protein or polypeptide involved in hemophilia, for example Factor VII, F8, F.IX, Factor X, GBA, GLA, IDS, IDUA, SMPD1 and/or functional fragments thereof. Also disclosed are methods of treating a disorder in which one or more proteins or lacking or deficient (e.g., a hemophilia or a lysosomal storage disease) using a cell as described herein and/or by modifying a cell (ex vivo or in vivo) as described herein to produce the one or more proteins lacking or deficient in the subject. Further described are compositions comprising nucleic acids encoding nucleases and donor molecules for modifying a cell, and methods for modifying the cell in vivo or ex vivo. Additionally, compositions comprising cells that have been modified by the methods and compositions of the invention are described.

The genomically-modified cells described herein can be modified via nuclease-mediated (ZFN, TALEN and/or CRISPR/Cas) targeted integration in the presence of the topoisomerase inhibitor(s) such that the frequency of transgene insertion is enhanced and the cells produce the protein in vivo. In certain embodiments, the methods further comprise inducing cells of the subject, particularly liver cells, to proliferate (enter the cell cycle), for example, by partial hepatectomy and/or by administration of one or more compounds that induce hepatic cells to undergo cell cycling. Subjects include but are not limited to humans, non-human primates, veterinary animals such as cats, dogs, rabbits, rats, mice, guinea pigs, cows, pigs, horses, goats and the like.

General

Practice of the methods, as well as preparation and use of the compositions disclosed herein employ, unless otherwise indicated, conventional techniques in molecular biology, biochemistry, chromatin structure and analysis, computational chemistry, cell culture, recombinant DNA and related fields as are within the skill of the art. These techniques are fully explained in the literature. See, for example, Sambrook et al. MOLECULAR CLONING: A LABORATORY MANUAL, Second edition, Cold Spring Harbor Laboratory Press, 1989 and Third edition, 2001; Ausubel et al., CURRENT PROTOCOLS IN MOLECULAR BIOLOGY, John Wiley & Sons, New York, 1987 and periodic updates; the series METHODS IN ENZYMOLOGY, Academic Press, San Diego; Wolffe, CHROMATIN STRUCTURE AND FUNCTION, Third edition, Academic Press, San Diego, 1998; METHODS IN ENZYMOLOGY, Vol. 304, "Chromatin" (P. M. Wassarman and A. P. Wolffe, eds.), Academic Press, San Diego, 1999; and METHODS IN MOLECULAR BIOLOGY, Vol. 119, "Chromatin Protocols" (P. B. Becker, ed.) Humana Press, Totowa, 1999.

Definitions

The terms "nucleic acid," "polynucleotide," and "oligonucleotide" are used interchangeably and refer to a deoxyribonucleotide or ribonucleotide polymer, in linear or circular conformation, and in either single- or double-stranded form. For the purposes of the present disclosure, these terms are not to be construed as limiting with respect to the length of a polymer. The terms can encompass known analogues of natural nucleotides, as well as nucleotides that are modified in the base, sugar and/or phosphate moieties (e.g., phosphorothioate backbones). In general, an analogue of a particular nucleotide has the same base-pairing specificity; i.e., an analogue of A will base-pair with T.

The terms "polypeptide," "peptide" and "protein" are used interchangeably to refer to a polymer of amino acid residues. The term also applies to amino acid polymers in which one or more amino acids are chemical analogues or modified derivatives of a corresponding naturally-occurring amino acids.

"Binding" refers to a sequence-specific, non-covalent interaction between macromolecules (e.g., between a protein and a nucleic acid). Not all components of a binding interaction need be sequence-specific (e.g., contacts with phosphate residues in a DNA backbone), as long as the interaction as a whole is sequence-specific. Such interactions are generally characterized by a dissociation constant ($K_d$) of $10^{-6}$ $M^{-1}$ or lower. "Affinity" refers to the strength of binding: increased binding affinity being correlated with a lower $K_d$.

A "binding protein" is a protein that is able to bind non-covalently to another molecule. A binding protein can bind to, for example, a DNA molecule (a DNA-binding protein), an RNA molecule (an RNA-binding protein) and/or a protein molecule (a protein-binding protein). In the case of a protein-binding protein, it can bind to itself (to form homodimers, homotrimers, etc.) and/or it can bind to one or more molecules of a different protein or proteins. A binding protein can have more than one type of binding activity. For example, zinc finger proteins have DNA-binding, RNA-binding and protein-binding activity.

A "zinc finger DNA binding protein" (or binding domain) is a protein, or a domain within a larger protein, that binds DNA in a sequence-specific manner through one or more zinc fingers, which are regions of amino acid sequence within the binding domain whose structure is stabilized through coordination of a zinc ion. The term zinc finger DNA binding protein is often abbreviated as zinc finger protein or ZFP.

A "TALE DNA binding domain" or "TALE" is a polypeptide comprising one or more TALE repeat domains/units. The repeat domains are involved in binding of the TALE to its cognate target DNA sequence. A single "repeat unit" (also referred to as a "repeat") is typically 33-35 amino acids in length and exhibits at least some sequence homology with other TALE repeat sequences within a naturally occurring TALE protein. See, e.g., U.S. Pat. No. 8,586,526.

Zinc finger and TALE binding domains can be "engineered" to bind to a predetermined nucleotide sequence, for example via engineering (altering one or more amino acids) of the recognition helix region of a naturally occurring zinc finger or TALE protein. Therefore, engineered DNA binding proteins (zinc fingers or TALEs) are proteins that are non-naturally occurring. Non-limiting examples of methods for engineering DNA-binding proteins are design and selection. A designed DNA binding protein is a protein not occurring in nature whose design/composition results principally from rational criteria. Rational criteria for design include application of substitution rules and computerized algorithms for processing information in a database storing information of existing ZFP and/or TALE designs and binding data. See, for example, U.S. Pat. Nos. 6,140,081; 6,453,242; 6,534,261; and 8,586,526 see also WO 98/53058; WO 98/53059; WO 98/53060; WO 02/016536 and WO 03/016496.

A "selected" zinc finger protein or TALE is a protein not found in nature whose production results primarily from an empirical process such as phage display, interaction trap or hybrid selection. See e.g., U.S. Pat. Nos. 5,789,538; 5,925, 523; 6,007,988; 6,013,453; 6,200,759; WO 95/19431; WO 96/06166; WO 98/53057; WO 98/54311; WO 00/27878; WO 01/60970 WO 01/88197 and WO 02/099084.

"TtAgo" is a prokaryotic Argonaute protein thought to be involved in gene silencing. TtAgo is derived from the bacteria *Thermus thermophilus*. See, e.g., Swarts et al, ibid, G. Sheng et al., (2013) *Proc. Natl. Acad. Sci. U.S.A.* 111, 652). A "TtAgo system" is all the components required including, for example, guide DNAs for cleavage by a TtAgo enzyme.

"Recombination" refers to a process of exchange of genetic information between two polynucleotides, including but not limited to, donor capture by non-homologous end joining (NHEJ) and homologous recombination. For the purposes of this disclosure, "homologous recombination (HR)" refers to the specialized form of such exchange that takes place, for example, during repair of double-strand breaks in cells via homology-directed repair mechanisms. This process requires nucleotide sequence homology, uses a "donor" molecule to template repair of a "target" molecule (i.e., the one that experienced the double-strand break), and is variously known as "non-crossover gene conversion" or "short tract gene conversion," because it leads to the transfer of genetic information from the donor to the target. Without wishing to be bound by any particular theory, such transfer can involve mismatch correction of heteroduplex DNA that forms between the broken target and the donor, and/or "synthesis-dependent strand annealing," in which the donor is used to resynthesize genetic information that will become part of the target, and/or related processes. Such specialized HR often results in an alteration of the sequence of the target molecule such that part or all of the sequence of the donor polynucleotide is incorporated into the target polynucleotide.

In the methods of the disclosure, one or more targeted nucleases as described herein create a double-stranded break in the target sequence (e.g., cellular chromatin) at a predetermined site, and a "donor" polynucleotide, having homology to the nucleotide sequence in the region of the break, can be introduced into the cell. The presence of the double-stranded break has been shown to facilitate integration of the donor sequence. The donor sequence may be physically integrated or, alternatively, the donor polynucleotide is used as a template for repair of the break via homologous recombination, resulting in the introduction of all or part of the nucleotide sequence as in the donor into the cellular chromatin. Thus, a first sequence in cellular chromatin can be altered and, in certain embodiments, can be converted into a sequence present in a donor polynucleotide. Thus, the use of the terms "replace" or "replacement" can be understood to represent replacement of one nucleotide sequence by another, (i.e., replacement of a sequence in the informational sense), and does not necessarily require physical or chemical replacement of one polynucleotide by another.

In any of the methods described herein, additional pairs of zinc-finger proteins or TALEN can be used for additional double-stranded cleavage of additional target sites within the cell.

In certain embodiments of methods for targeted recombination and/or replacement and/or alteration of a sequence in a region of interest in cellular chromatin, a chromosomal sequence is altered by homologous recombination with an exogenous "donor" nucleotide sequence. Such homologous recombination is stimulated by the presence of a double-stranded break in cellular chromatin, if sequences homologous to the region of the break are present.

In any of the methods described herein, the first nucleotide sequence (the "donor sequence") can contain sequences that are homologous, but not identical, to genomic sequences in the region of interest, thereby stimulating homologous recombination to insert a non-identical sequence in the region of interest. Thus, in certain embodiments, portions of the donor sequence that are homologous to sequences in the region of interest exhibit between about 80 to 99% (or any integer therebetween) sequence identity to the genomic sequence that is replaced. In other embodiments, the homology between the donor and genomic sequence is higher than 99%, for example if only 1 nucleotide differs as between donor and genomic sequences of over 100 contiguous base pairs. In certain cases, a non-homologous portion of the donor sequence can contain sequences not present in the region of interest, such that new sequences are introduced into the region of interest. In these instances, the non-homologous sequence is generally flanked by sequences of 50-1,000 base pairs (or any integral value therebetween) or any number of base pairs greater than 1,000, that are homologous or identical to sequences in the region of interest. In other embodiments, the donor sequence is non-homologous to the first sequence, and is inserted into the genome by non-homologous recombination mechanisms.

Any of the methods described herein can be used for partial or complete inactivation of one or more target sequences in a cell by targeted integration of donor sequence that disrupts expression of the gene(s) of interest. Cell lines with partially or completely inactivated genes are also provided.

Furthermore, the methods of targeted integration as described herein can also be used to integrate one or more exogenous sequences. The exogenous nucleic acid sequence can comprise, for example, one or more genes or cDNA molecules, or any type of coding or noncoding sequence, as well as one or more control elements (e.g., promoters). In addition, the exogenous nucleic acid sequence may produce one or more RNA molecules (e.g., small hairpin RNAs (shRNAs), inhibitory RNAs (RNAis), microRNAs (miRNAs), etc.).

"Cleavage" refers to the breakage of the covalent backbone of a DNA molecule. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. DNA cleavage can result in the production of either blunt ends or staggered ends. In certain embodiments, fusion polypeptides are used for targeted double-stranded DNA cleavage.

A "cleavage half-domain" is a polypeptide sequence which, in conjunction with a second polypeptide (either identical or different) forms a complex having cleavage activity (preferably double-strand cleavage activity). The terms "first and second cleavage half-domains;" "+ and − cleavage half-domains" and "right and left cleavage half-domains" are used interchangeably to refer to pairs of cleavage half-domains that dimerize.

An "engineered cleavage half-domain" is a cleavage half-domain that has been modified so as to form obligate heterodimers with another cleavage half-domain (e.g., another engineered cleavage half-domain). See, also, U.S. Pat. Nos. 7,914,796; 8,034,598; and 8,623,618; incorporated herein by reference in their entireties.

The term "sequence" refers to a nucleotide sequence of any length, which can be DNA or RNA; can be linear, circular or branched and can be either single-stranded or double stranded. The term "donor sequence" refers to a nucleotide sequence that is inserted into a genome. A donor sequence can be of any length, for example between 2 and 10,000 nucleotides in length (or any integer value therebetween or thereabove), preferably between about 100 and 1,000 nucleotides in length (or any integer therebetween), more preferably between about 200 and 500 nucleotides in length.

"Chromatin" is the nucleoprotein structure comprising the cellular genome. Cellular chromatin comprises nucleic acid, primarily DNA, and protein, including histones and non-histone chromosomal proteins. The majority of eukaryotic cellular chromatin exists in the form of nucleosomes, wherein a nucleosome core comprises approximately 150 base pairs of DNA associated with an octamer comprising two each of histones H2A, H2B, H3 and H4; and linker DNA (of variable length depending on the organism) extends between nucleosome cores. A molecule of histone H1 is generally associated with the linker DNA. For the purposes of the present disclosure, the term "chromatin" is meant to encompass all types of cellular nucleoprotein, both prokaryotic and eukaryotic. Cellular chromatin includes both chromosomal and episomal chromatin.

A "chromosome," is a chromatin complex comprising all or a portion of the genome of a cell. The genome of a cell is often characterized by its karyotype, which is the collection of all the chromosomes that comprise the genome of the cell. The genome of a cell can comprise one or more chromosomes.

An "episome" is a replicating nucleic acid, nucleoprotein complex or other structure comprising a nucleic acid that is not part of the chromosomal karyotype of a cell. Examples of episomes include plasmids and certain viral genomes.

A "target site" or "target sequence" is a nucleic acid sequence that defines a portion of a nucleic acid to which a binding molecule will bind, provided sufficient conditions for binding exist.

An "exogenous" molecule is a molecule that is not normally present in a cell, but can be introduced into a cell by one or more genetic, biochemical or other methods. "Normal presence in the cell" is determined with respect to the particular developmental stage and environmental conditions of the cell. Thus, for example, a molecule that is present only during embryonic development of muscle is an exogenous molecule with respect to an adult muscle cell. Similarly, a molecule induced by heat shock is an exogenous molecule with respect to a non-heat-shocked cell. An exogenous molecule can comprise, for example, a functioning version of a malfunctioning endogenous molecule or a malfunctioning version of a normally-functioning endogenous molecule.

An exogenous molecule can be, among other things, a small molecule, such as is generated by a combinatorial chemistry process, or a macromolecule such as a protein, nucleic acid, carbohydrate, lipid, glycoprotein, lipoprotein, polysaccharide, any modified derivative of the above molecules, or any complex comprising one or more of the above molecules. Nucleic acids include DNA and RNA, can be single- or double-stranded; can be linear, branched or circular; and can be of any length. Nucleic acids include those capable of forming duplexes, as well as triplex-forming nucleic acids. See, for example, U.S. Pat. Nos. 5,176,996 and 5,422,251. Proteins include, but are not limited to, DNA-binding proteins, transcription factors, chromatin remodeling factors, methylated DNA binding proteins, polymerases, methylases, demethylases, acetylases, deacetylases, kinases, phosphatases, integrases, recombinases, ligases, topoisomerases, gyrases and helicases.

An exogenous molecule can be the same type of molecule as an endogenous molecule, e.g., an exogenous protein or nucleic acid. For example, an exogenous nucleic acid can comprise an infecting viral genome, a plasmid or episome introduced into a cell, or a chromosome that is not normally present in the cell. Methods for the introduction of exogenous molecules into cells are known to those of skill in the art and include, but are not limited to, lipid-mediated transfer (i.e., liposomes, including neutral and cationic lipids), electroporation, direct injection, cell fusion, particle bombardment, calcium phosphate co-precipitation, DEAE-dextran-mediated transfer and viral vector-mediated transfer. An exogenous molecule can also be the same type of molecule as an endogenous molecule but derived from a different species than the cell is derived from. For example, a human nucleic acid sequence may be introduced into a cell line originally derived from a mouse or hamster.

By contrast, an "endogenous" molecule is one that is normally present in a particular cell at a particular developmental stage under particular environmental conditions. For example, an endogenous nucleic acid can comprise a chromosome, the genome of a mitochondrion, chloroplast or other organelle, or a naturally-occurring episomal nucleic acid. Additional endogenous molecules can include proteins, for example, transcription factors and enzymes.

A "fusion" molecule is a molecule in which two or more subunit molecules are linked, preferably covalently. The subunit molecules can be the same chemical type of molecule, or can be different chemical types of molecules. Examples of the first type of fusion molecule include, but are not limited to, fusion proteins (for example, a fusion between a ZFP or TALE DNA-binding domain and one or more activation domains) and fusion nucleic acids (for example, a nucleic acid encoding the fusion protein described supra). Examples of the second type of fusion molecule include, but are not limited to, a fusion between a triplex-forming nucleic acid and a polypeptide, and a fusion between a minor groove binder and a nucleic acid.

Expression of a fusion protein in a cell can result from delivery of the fusion protein to the cell or by delivery of a polynucleotide encoding the fusion protein to a cell, wherein the polynucleotide is transcribed, and the transcript is translated, to generate the fusion protein. Trans-splicing, polypeptide cleavage and polypeptide ligation can also be involved in expression of a protein in a cell. Methods for polynucleotide and polypeptide delivery to cells are presented elsewhere in this disclosure.

A "gene," for the purposes of the present disclosure, includes a DNA region encoding a gene product (see infra), as well as all DNA regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions.

"Gene expression" refers to the conversion of the information, contained in a gene, into a gene product. A gene product can be the direct transcriptional product of a gene (e.g., mRNA, tRNA, rRNA, antisense RNA, ribozyme, structural RNA or any other type of RNA) or a protein produced by translation of an mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation.

"Modulation" of gene expression refers to a change in the activity of a gene. Modulation of expression can include, but is not limited to, gene activation and gene repression. Genome editing (e.g., cleavage, alteration, inactivation, random mutation) can be used to modulate expression. Gene inactivation refers to any reduction in gene expression as compared to a cell that does not include a ZFP as described herein. Thus, gene inactivation may be partial or complete.

A "region of interest" is any region of cellular chromatin, such as, for example, a gene or a non-coding sequence within or adjacent to a gene, in which it is desirable to bind an exogenous molecule. Binding can be for the purposes of targeted DNA cleavage and/or targeted recombination. A region of interest can be present in a chromosome, an episome, an organellar genome (e.g., mitochondrial, chloroplast), or an infecting viral genome, for example. A region of interest can be within the coding region of a gene, within transcribed non-coding regions such as, for example, leader sequences, trailer sequences or introns, or within non-transcribed regions, either upstream or downstream of the coding region. A region of interest can be as small as a single nucleotide pair or up to 2,000 nucleotide pairs in length, or any integral value of nucleotide pairs.

"Eukaryotic" cells include, but are not limited to, fungal cells (such as yeast), plant cells, animal cells, mammalian cells and human cells (e.g., T-cells).

The terms "operative linkage" and "operatively linked" (or "operably linked") are used interchangeably with reference to a juxtaposition of two or more components (such as sequence elements), in which the components are arranged such that both components function normally and allow the possibility that at least one of the components can mediate a function that is exerted upon at least one of the other components. By way of illustration, a transcriptional regulatory sequence, such as a promoter, is operatively linked to a coding sequence if the transcriptional regulatory sequence controls the level of transcription of the coding sequence in response to the presence or absence of one or more transcriptional regulatory factors. A transcriptional regulatory sequence is generally operatively linked in cis with a coding sequence, but need not be directly adjacent to it. For example, an enhancer is a transcriptional regulatory sequence that is operatively linked to a coding sequence, even though they are not contiguous.

With respect to fusion polypeptides, the term "operatively linked" can refer to the fact that each of the components performs the same function in linkage to the other component as it would if it were not so linked. For example, with respect to a fusion polypeptide in which a ZFP DNA-binding domain is fused to an activation domain, the ZFP DNA-binding domain and the activation domain are in operative linkage if, in the fusion polypeptide, the ZFP DNA-binding domain portion is able to bind its target site and/or its binding site, while the activation domain is able to upregulate gene expression. When a fusion polypeptide in which a ZFP DNA-binding domain is fused to a cleavage domain, the ZFP DNA-binding domain and the cleavage domain are in operative linkage if, in the fusion polypeptide, the ZFP DNA-binding domain portion is able to bind its target site and/or its binding site, while the cleavage domain is able to cleave DNA in the vicinity of the target site.

A "functional fragment" of a protein, polypeptide or nucleic acid is a protein, polypeptide or nucleic acid whose sequence is not identical to the full-length protein, polypeptide or nucleic acid, yet retains the same function as the full-length protein, polypeptide or nucleic acid. A functional fragment can possess more, fewer, or the same number of residues as the corresponding native molecule, and/or can contain one or more amino acid or nucleotide substitutions. Methods for determining the function of a nucleic acid (e.g., coding function, ability to hybridize to another nucleic acid) are well-known in the art. Similarly, methods for determining protein function are well-known. For example, the DNA-binding function of a polypeptide can be determined, for example, by filter-binding, electrophoretic mobility-shift, or immunoprecipitation assays. DNA cleavage can be assayed by gel electrophoresis. See Ausubel et al., supra. The ability of a protein to interact with another protein can be determined, for example, by co-immunoprecipitation, two-hybrid assays or complementation, both genetic and biochemical. See, for example, Fields et al. (1989) *Nature* 340:245-246; U.S. Pat. No. 5,585,245 and PCT WO 98/44350.

A "vector" is capable of transferring gene sequences to target cells. Typically, "vector construct," "expression vector," and "gene transfer vector," mean any nucleic acid construct capable of directing the expression of a gene of interest and which can transfer gene sequences to target cells. Thus, the term includes cloning, and expression vehicles, as well as integrating vectors.

A "safe harbor" locus is a locus within the genome wherein a gene may be inserted without any deleterious effects on the host cell. Most beneficial is a safe harbor locus in which expression of the inserted gene sequence is not perturbed by any read-through expression from neighboring genes. Non-limiting examples of safe harbor loci that are targeted by nuclease(s) include CCR5, CCR5, HPRT, AAVS1, Rosa and albumin. See, e.g., U.S. Pat. Nos. 7,951,925; 8,771,985; 8,110,379; 7,951,925; U.S. Publication Nos. 20100218264; 20110265198; 20130137104; 20130122591; 20130177983; 20130177960; 20150056705 and 20150159172.

Compounds to Increase Transgene Integration

Topoisomerase Inhibitors

Any inhibitor(s) of topoisomerase may be used in the practice of the present invention. The inhibitor may inhibit Type I (nicking enzyme) and/or Type II topoisomerase (double strand break). Non limiting examples of suitable topoisomerase inhibitors include, camptothecin, etoposide (a type II topoisomerase inhibitor) as well as doxorubicin, cisplatin, topotecan, irinotecan, tenipopside, mitoxantrone, etoposide phosphate, and topotecan hydrochloride.

Topoisomerase inhibitors are often used for oncology patients. Doses suitable for these compounds (doxorubicin for example) will be less than typically used in vitro (e.g. see Svensson (1995) *Cancer Research* 55: 2357) since the goal is to selectively increase DNA nicks and breaks in the most heavily transcribed genes. Concentrations to be used in vitro may be 1 µM or less, 600 nM or less, 300 nM or less, 100 nM or less, 50 nM or less, 10, 9, 8, 7, 6, 5, 4, 3 2, or 1 nM or less. For in vivo dosing, concentrations will also be less than typically used for a patient, e.g. 100 mg/m$^2$ or less, 50 mg/m$^2$ or less, 25 mg/m$^2$ or less, 10 mg/m$^2$ or less, 5 mg/m$^2$ or less, or 4, 3, 2, 1, 0.5, 0.3, 0.1 mg/m$^2$ or less.

R-Loop Stabilizers and R-Loop Repair Inhibitors

R-loop stabilizers are used alone or in combination with the other compounds described in this method. R loop repair inhibitors and also contemplated. Suitable R-loop stabilizers and R-loop repair inhibitors include compounds designed to inhibit RNA-DNA helicases, AQR, XAB2, PRP19, CCDC16, PPiE, hISY1, (R-loop stabilizers) and XPF, XPG, XPA, XPB, XPD, and CSB inhibitors. Suitable inhibitors include compounds designed to inhibit the expression of these genes (transcription factors, RNAis) as well as compounds designed to act upon the enzymes themselves (small molecule or antibody enzyme inhibitors).

TC-NER Pathway Regulators

The NER pathway resolves numerous DNA lesions, particularly base modifications that distort the normal helical structure of duplex DNA. The NER response involves four primary steps: i) recognition of the damage, ii) incision on both sides of the lesion and removal of the damage-containing oligonucleotide fragment, iii) gap-filling synthesis to restore a damage-free DNA duplex, and iv) ligation to seal the remaining nick. Defects in NER are genetically linked to a group of associated autosomal recessive human diseases (discussed in greater detail below): xeroderma pigmentosum (XP), Cockayne syndrome (CS) and a photosensitive form of trichothiodystrophy (TTD). Each of these disorders is characterized by extreme UV radiation sensitivity, and in some cases, neurological dysfunction is observed. The global NER pathway, GG-NER is used throughout the genome while the TC-NER pathway specifically deals with lesions on the transcribed strand of DNA that block RNA polymerase (RNAP) progression. This arrested RNAP serves as a critical signal via an unknown mechanism to engage the CS proteins, CSA and CSB, which facilitate the eventual removal of the damage and restart of transcription. After recruitment of the TFIIH complex which contains ten subunits, including two helicases XPB (3'-5') and XPD (5'-3'). Through the activity of the helicase subunits, TFIIH promotes opening of the DNA duplex around the lesion, creating a "bubble" platform for recruitment of XPA and replication protein A (RPA), and assembly of the pre-incision complex. XPA promotes the release of the TFIIH component, the cyclin-dependent kinase (CDK)-activating kinase (CAK) sub-complex, and the association of RPA with the single-stranded damaged DNA. The dissociation of CAK is thought to facilitate the recruitment of the XPF-excision repair cross complementing 1 (ERCC1) complex and XPG, as well as the release of XPC-RAD23B. The XPF-ERCC1 complex is recruited to the lesion via a direct interaction with XPA, while XPG is specifically engaged via an interaction with TFIIH and stabilization of the pre-incision complex. The two endonucleases, XPF-ERCC1 and XPG, are then responsible for carrying out incision 5' and 3', respectively, to the DNA damage. After the dual incision event and removal of the damage-containing oligonucleotide fragment, DNA polymerases δ, ε or κ carry out gap-filling repair synthesis in cooperation with replication factor C (RFC) and proliferating cellular nuclear antigen (PCNA). Finally, the nick is sealed in dividing cells by either a X-ray repair cross-complementing protein 1 (XRCC1)-DNA ligase III (LIG3) or a flap endonuclease 1 (FEN1)-DNA ligase I (LIG1) complex, or in non-dividing cells by XRCC1-LIG3α (see for example (Iyama et al (2013) *DNA Repair.* 12(8):620). Components of the TC-NER (transcription coupled) pathway like XPF, XPG, XPA, XPB, XPD and CSB have been shown to aid the generation of DSBs.

Thus, in certain embodiments, one or more up regulators of the TC-NER pathway is(are) used to increase targeted integration.

Nucleases

The methods and compositions described herein may also make use of one or more nucleases that are useful in integration of a transgene (e.g., sequence encoding a functional protein that is lacking, deficient or aberrantly expressed in a subject with a disease or disorder such as a protein that is lacking or deficient in a subject with an LSD and/or a clotting factor (e.g., F8 and/or F.IX) protein in the genome of a cell from or in a subject with hemophilia A or B). In certain embodiments, the nuclease is naturally occurring. In other embodiments, the nuclease is non-naturally occurring, i.e., engineered in the DNA-binding molecule (domain) and/or cleavage domain. For example, the DNA-binding domain of a naturally-occurring nuclease may be altered to bind to a selected target site (e.g., a meganuclease that has been engineered to bind to site different than the cognate binding site). In other embodiments, the nuclease comprises heterologous DNA-binding molecule(s) and cleavage domains (e.g., zinc finger nucleases; TAL-effector domain DNA binding proteins; meganuclease DNA-binding domains with heterologous cleavage domains) and/or a CRISPR/Cas system utilizing an engineered single guide RNA).

The nuclease(s) can induce a double-stranded (DSB) or single-stranded break (nick) in the target DNA. See, e.g., U.S. Pat. Nos. 8,703,489 and 8,932,814. In some embodiments, two nickases are used to create a DSB by introducing two nicks.

A. DNA-Binding Domains

Any DNA-binding domain can be used in the compositions and methods disclosed herein, including but not limited to a zinc finger DNA-binding domain, a TALE DNA binding domain, the DNA-binding portion (sgRNA) of a CRISPR/Cas nuclease, or a DNA-binding domain from a meganuclease.

In certain embodiments, the nuclease is a naturally occurring or engineered (non-naturally occurring) meganuclease (homing endonuclease). Exemplary homing endonucleases include I-SceI, I-CeuI, PI-PspI, PI-Sce, I-SceIV, I-CsmI, I-PanI, I-SceII, I-PpoI, I-SceIII, I-CreI, I-TevI, I-TevII and I-TevIII. Their recognition sequences are known. See also U.S. Pat. Nos. 5,420,032; 6,833,252; Belfort et al. (1997) *Nucleic Acids Res.* 25:3379-3388; Duj on et al. (1989) *Gene* 82:115-118; Perler et al. (1994) *Nucleic Acids Res.* 22, 1125-1127; Jasin (1996) *Trends Genet.* 12:224-228; Gimble et al. (1996) *J. Mol. Biol.* 263:163-180; Argast et al. (1998) *J. Mol. Biol.* 280:345-353 and the New England Biolabs catalogue. Engineered meganucleases are described for example in U.S. Patent Publication No. 20070117128. The DNA-binding domains of the homing endonucleases and meganucleases may be altered in the context of the nuclease as a whole (i.e., such that the nuclease includes the cognate cleavage domain) or may be fused to a heterologous cleavage domain. DNA-binding domains from meganucleases may also exhibit nuclease activity (e.g., cTALENs).

In other embodiments, the DNA-binding domain comprises a naturally occurring or engineered (non-naturally occurring) TAL effector DNA binding domain. See, e.g., U.S. Pat. No. 8,586,526, incorporated by reference in its entirety herein. The plant pathogenic bacteria of the genus *Xanthomonas* are known to cause many diseases in important crop plants. Pathogenicity of *Xanthomonas* depends on a conserved type III secretion (T3 S) system which injects more than 25 different effector proteins into the plant cell. Among these injected proteins are transcription activator-like (TAL) effectors which mimic plant transcriptional activators and manipulate the plant transcriptome (see Kay et al (2007) *Science* 318:648-651). These proteins contain a DNA binding domain and a transcriptional activation domain. One of the most well characterized TAL-effectors is AvrBs3 from *Xanthomonas campestgris* pv. *Vesicatoria* (see Bonas et al (1989) *Mol Gen Genet* 218: 127-136 and WO2010079430). TAL-effectors contain a centralized domain of tandem repeats, each repeat containing approximately 34 amino acids, which are key to the DNA binding specificity of these proteins. In addition, they contain a nuclear localization sequence and an acidic transcriptional activation domain (for a review see Schornack S, et al (2006) *J Plant Physiol* 163(3): 256-272). In addition, in the phytopathogenic bacteria *Ralstonia solanacearum* two genes, designated brg11 and hpx17 have been found that are homologous to the AvrBs3 family of *Xanthomonas* in the *R. solanacearum* biovar 1 strain GMI1000 and in the biovar 4 strain RS1000 (See Heuer et al (2007) *Appl and Envir Micro* 73(13): 4379-4384). These genes are 98.9% identical in nucleotide sequence to each other but differ by a deletion of 1,575 base pairs in the repeat domain of hpx17. However, both gene products have less than 40% sequence identity with AvrBs3 family proteins of *Xanthomonas*. See, e.g., U.S. Pat. No. 8,586,526, incorporated by reference in its entirety herein.

Specificity of these TAL effectors depends on the sequences found in the tandem repeats. The repeated sequence comprises approximately 102 base pairs and the repeats are typically 91-100% homologous with each other (Bonas et al, ibid). Polymorphism of the repeats is usually located at positions 12 and 13 and there appears to be a one-to-one correspondence between the identity of the hypervariable diresidues (the repeat variable diresidue or RVD region) at positions 12 and 13 with the identity of the contiguous nucleotides in the TAL-effector's target sequence (see Moscou and Bogdanove, (2009) *Science* 326:1501 and Boch at (2009) *Science* 326:1509-1512). Experimentally, the natural code for DNA recognition of these TAL-effectors has been determined such that an HD sequence at positions 12 and 13 (Repeat Variable Diresidue or RVD) leads to a binding to cytosine (C), NG binds to T, NI to A, C, G or T, NN binds to A or G, and ING binds to T. These DNA binding repeats have been assembled into proteins with new combinations and numbers of repeats, to make artificial transcription factors that are able to interact with new sequences and activate the expression of a non-endogenous reporter gene in plant cells (Boch et al, ibid). Engineered TAL proteins have been linked to a FokI cleavage half domain to yield a TAL effector domain nuclease fusion (TALEN), including TALENs with atypical RVDs. See, e.g., U.S. Pat. No. 8,586,526.

In some embodiments, the TALEN comprises an endonuclease (e.g., FokI) cleavage domain or cleavage half-domain. In other embodiments, the TALE-nuclease is a mega TAL. These mega TAL nucleases are fusion proteins comprising a TALE DNA binding domain and a meganuclease cleavage domain. The meganuclease cleavage domain is active as a monomer and does not require dimerization for activity. (See Boissel et al., (2013) *Nucl Acid Res:* 1-13, doi: 10.1093/nar/gkt1224).

In still further embodiments, the nuclease comprises a compact TALEN. These are single chain fusion proteins linking a TALE DNA binding domain to a TevI nuclease domain. The fusion protein can act as either a nickase localized by the TALE region, or can create a double strand break, depending upon where the TALE DNA binding domain is located with respect to the TevI nuclease domain (see Beurdeley et al (2013) *Nat Comm:* 1-8 DOI: 10.1038/ncomms2782). In addition, the nuclease domain may also exhibit DNA-binding functionality. Any TALENs may be used in combination with additional TALENs (e.g., one or more TALENs (cTALENs or FokI-TALENs) with one or more mega-TALEs.

In certain embodiments, the DNA binding domain comprises a zinc finger protein. Preferably, the zinc finger protein is non-naturally occurring in that it is engineered to bind to a target site of choice. See, for example, Beerli et al. (2002) *Nature Biotechnol.* 20:135-141; Pabo et al. (2001) *Ann. Rev. Biochem.* 70:313-340; Isalan et al. (2001) *Nature Biotechnol.* 19:656-660; Segal et al. (2001) *Curr. Opin. Biotechnol.* 12:632-637; Choo et al. (2000) *Curr. Opin. Struct. Biol.* 10:411-416; U.S. Pat. Nos. 6,453,242; 6,534,261; 6,599,692; 6,503,717; 6,689,558; 7,030,215; 6,794,136; 7,067,317; 7,262,054; 7,070,934; 7,361,635; 7,253, 273; and U.S. Patent Publication Nos. 2005/0064474; 2007/0218528; 2005/0267061, all incorporated herein by reference in their entireties.

An engineered zinc finger binding domain can have a novel binding specificity, compared to a naturally-occurring zinc finger protein. Engineering methods include, but are not limited to, rational design and various types of selection. Rational design includes, for example, using databases comprising triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, for example, co-owned U.S. Pat. Nos. 6,453,242 and 6,534,261, incorporated by reference herein in their entireties.

Exemplary selection methods, including phage display and two-hybrid systems, are disclosed in U.S. Pat. Nos. 5,789,538; 5,925,523; 6,007,988; 6,013,453; 6,410,248; 6,140,466; 6,200,759; and 6,242,568; as well as WO 98/37186; WO 98/53057; WO 00/27878; WO 01/88197 and GB 2,338,237. In addition, enhancement of binding specificity for zinc finger binding domains has been described, for example, in co-owned WO 02/077227.

In addition, as disclosed in these and other references, zinc finger domains and/or multi-fingered zinc finger proteins may be linked together using any suitable linker sequences, including for example, linkers of 5 or more amino acids in length. See, also, U.S. Pat. Nos. 6,479,626; 6,903,185; and 7,153,949 for exemplary linker sequences 6 or more amino acids in length. The proteins described herein may include any combination of suitable linkers between the individual zinc fingers of the protein.

Selection of target sites; ZFPs and methods for design and construction of fusion proteins (and polynucleotides encoding same) are known to those of skill in the art and described in detail in U.S. Pat. Nos. 6,140,081; 5,789,538; 6,453,242; 6,534,261; 5,925,523; 6,007,988; 6,013,453; 6,200,759; WO 95/19431; WO 96/06166; WO 98/53057; WO 98/54311; WO 00/27878; WO 01/60970 WO 01/88197; WO 02/099084; WO 98/53058; WO 98/53059; WO 98/53060; WO 02/016536 and WO 03/016496.

In addition, as disclosed in these and other references, zinc finger domains and/or multi-fingered zinc finger proteins may be linked together using any suitable linker sequences, including for example, linkers of 5 or more amino acids in length. See, also, U.S. Pat. Nos. 6,479,626; 6,903,185; and 7,153,949 for exemplary linker sequences 6 or more amino acids in length. The proteins described herein may include any combination of suitable linkers between the individual zinc fingers of the protein.

In certain embodiments, the DNA-binding domain is part of a CRISPR/Cas nuclease system, including a single guide RNA (sgRNA) that binds to DNA. See, e.g., U.S. Pat. No. 8,697,359 and U.S. Patent Publication Nos. 20150056705 and 20150159172. The CRISPR (clustered regularly interspaced short palindromic repeats) locus, which encodes RNA components of the system, and the cas (CRISPR-associated) locus, which encodes proteins (Jansen et al., 2002. *Mol. Microbiol.* 43: 1565-1575; Makarova et al., 2002. *Nucleic Acids Res.* 30: 482-496; Makarova et al., 2006. *Biol. Direct* 1: 7; Haft et al., 2005. *PLoS Comput. Biol.* 1: e60) make up the gene sequences of the CRISPR/Cas nuclease system. CRISPR loci in microbial hosts contain a combination of CRISPR-associated (Cas) genes as well as non-coding RNA elements capable of programming the specificity of the CRISPR-mediated nucleic acid cleavage.

The Type II CRISPR is one of the most well characterized systems and carries out targeted DNA double-strand break in four sequential steps. First, two non-coding RNA, the pre-crRNA array and tracrRNA, are transcribed from the CRISPR locus. Second, tracrRNA hybridizes to the repeat regions of the pre-crRNA and mediates the processing of pre-crRNA into mature crRNAs containing individual spacer sequences. Third, the mature crRNA:tracrRNA complex directs functional domain (e.g., nuclease such as Cas) to the target DNA via Watson-Crick base-pairing between the spacer on the crRNA and the protospacer on the target DNA next to the protospacer adjacent motif (PAM), an additional requirement for target recognition. Finally, Cas9 mediates cleavage of target DNA to create a double-stranded break within the protospacer. Activity of the CRISPR/Cas system comprises of three steps: (i) insertion of alien DNA sequences into the CRISPR array to prevent future attacks, in a process called 'adaptation', (ii) expression of the relevant proteins, as well as expression and processing of the array, followed by (iii) RNA-mediated interference with the alien nucleic acid. Thus, in the bacterial cell, several of the so-called 'Cas' proteins are involved with the natural function of the CRISPR/Cas system and serve roles in functions such as insertion of the alien DNA etc.

In certain embodiments, Cas protein may be a "functional derivative" of a naturally occurring Cas protein. A "functional derivative" of a native sequence polypeptide is a compound having a qualitative biological property in common with a native sequence polypeptide. "Functional derivatives" include, but are not limited to, fragments of a native sequence and derivatives of a native sequence polypeptide and its fragments, provided that they have a biological activity in common with a corresponding native sequence polypeptide. A biological activity contemplated herein is the ability of the functional derivative to hydrolyze a DNA substrate into fragments. The term "derivative" encompasses both amino acid sequence variants of polypeptide, covalent modifications, and fusions thereof such as derivative Cas proteins. Suitable derivatives of a Cas polypeptide or a fragment thereof include but are not limited to mutants, fusions, covalent modifications of Cas protein or a fragment thereof. Cas protein, which includes Cas protein or a fragment thereof, as well as derivatives of Cas protein or a fragment thereof, may be obtainable from a cell or synthesized chemically or by a combination of these two procedures. The cell may be a cell that naturally produces Cas protein, or a cell that naturally produces Cas protein and is genetically engineered to produce the endogenous Cas protein at a higher expression level or to produce a Cas protein from an exogenously introduced nucleic acid, which nucleic acid encodes a Cas that is same or different from the endogenous Cas. In some case, the cell does not naturally produce Cas protein and is genetically engineered to produce a Cas protein. In some embodiments, the Cas protein is a small Cas9 ortholog for delivery via an AAV vector (Ran et al (2015) *Nature* 510, p. 186).

In some embodiments, the DNA binding domain is part of a TtAgo system (see Swarts et al, ibid; Sheng et al, ibid). In eukaryotes, gene silencing is mediated by the Argonaute (Ago) family of proteins. In this paradigm, Ago is bound to small (19-31 nt) RNAs. This protein-RNA silencing complex recognizes target RNAs via Watson-Crick base pairing between the small RNA and the target and endonucleolytically cleaves the target RNA (Vogel (2014) *Science* 344: 972-973). In contrast, prokaryotic Ago proteins bind to small single-stranded DNA fragments and likely function to detect and remove foreign (often viral) DNA (Yuan et al., (2005)

*Mol. Cell* 19, 405; Olovnikov, et al. (2013) *Mol. Cell* 51, 594; Swarts et al., ibid). Exemplary prokaryotic Ago proteins include those from *Aquifex aeolicus, Rhodobacter sphaeroides,* and *Thermus thermophilus.*

One of the most well-characterized prokaryotic Ago protein is the one from *T thermophilus* (TtAgo; Swarts et al. ibid). TtAgo associates with either 15 nt or 13-25 nt single-stranded DNA fragments with 5' phosphate groups. This "guide DNA" bound by TtAgo serves to direct the protein-DNA complex to bind a Watson-Crick complementary DNA sequence in a third-party molecule of DNA. Once the sequence information in these guide DNAs has allowed identification of the target DNA, the TtAgo-guide DNA complex cleaves the target DNA. Such a mechanism is also supported by the structure of the TtAgo-guide DNA complex while bound to its target DNA (G. Sheng et al., ibid). Ago from *Rhodobacter sphaeroides* (RsAgo) has similar properties (Olivnikov et al. ibid).

Exogenous guide DNAs of arbitrary DNA sequence can be loaded onto the TtAgo protein (Swarts et al. ibid.). Since the specificity of TtAgo cleavage is directed by the guide DNA, a TtAgo-DNA complex formed with an exogenous, investigator-specified guide DNA will therefore direct TtAgo target DNA cleavage to a complementary investigator-specified target DNA. In this way, one may create a targeted double-strand break in DNA. Use of the TtAgo-guide DNA system (or orthologous Ago-guide DNA systems from other organisms) allows for targeted cleavage of genomic DNA within cells. Such cleavage can be either single- or double-stranded. For cleavage of mammalian genomic DNA, it would be preferable to use of a version of TtAgo codon optimized for expression in mammalian cells. Further, it might be preferable to treat cells with a TtAgo-DNA complex formed in vitro where the TtAgo protein is fused to a cell-penetrating peptide. Further, it might be preferable to use a version of the TtAgo protein that has been altered via mutagenesis to have improved activity at 37° C. Ago-RNA-mediated DNA cleavage could be used to affect a panopoly of outcomes including gene knock-out, targeted gene addition, gene correction, targeted gene deletion using techniques standard in the art for exploitation of DNA breaks.

Thus, the nuclease comprises a DNA-binding domain in that specifically binds to a target site in any gene into which it is desired to insert a donor (transgene).

In certain embodiments, the nuclease(s) target an albumin gene.

B. Cleavage Domains

Any suitable cleavage domain can be operatively linked to a DNA-binding domain to form a nuclease, such as a zinc finger nuclease, a TALEN, or a CRISPR/Cas nuclease system. See, e.g., U.S. Pat. Nos. 7,951,925; 8,110,379 and 8,586,526; U.S. Publication Nos. 20080159996; 201000218264; 20120017290; 20110265198; 20130137104; 20130122591; 20130177983; 20130177960; 20150056705 and 20150159172.

As noted above, the cleavage domain may be heterologous to the DNA-binding domain, for example a zinc finger DNA-binding domain and a cleavage domain from a nuclease or a TALEN DNA-binding domain and a cleavage domain, or meganuclease DNA-binding domain and cleavage domain from a different nuclease. Heterologous cleavage domains can be obtained from any endonuclease or exonuclease. Exemplary endonucleases from which a cleavage domain can be derived include, but are not limited to, restriction endonucleases and homing endonucleases. See, for example, 2002-2003 Catalogue, New England Biolabs, Beverly, Mass.; and Belfort et al. (1997) *Nucleic Acids Res.* 25:3379-3388. Additional enzymes which cleave DNA are known (e.g., 51 Nuclease; mung bean nuclease; pancreatic DNase I; micrococcal nuclease; yeast HO endonuclease; see also Linn et al. (eds.) *Nucleases,* Cold Spring Harbor Laboratory Press, 1993). One or more of these enzymes (or functional fragments thereof) can be used as a source of cleavage domains and cleavage half-domains.

Similarly, a cleavage half-domain can be derived from any nuclease or portion thereof, as set forth above, that requires dimerization for cleavage activity. In general, two fusion proteins are required for cleavage if the fusion proteins comprise cleavage half-domains. Alternatively, a single protein comprising two cleavage half-domains can be used. The two cleavage half-domains can be derived from the same endonuclease (or functional fragments thereof), or each cleavage half-domain can be derived from a different endonuclease (or functional fragments thereof). In addition, the target sites for the two fusion proteins are preferably disposed, with respect to each other, such that binding of the two fusion proteins to their respective target sites places the cleavage half-domains in a spatial orientation to each other that allows the cleavage half-domains to form a functional cleavage domain, e.g., by dimerizing. Thus, in certain embodiments, the near edges of the target sites are separated by 5-8 nucleotides or by 15-18 nucleotides. However any number of nucleotides or nucleotide pairs can intervene between two target sites (e.g., from 2 to 50 nucleotide pairs or more). In general, the site of cleavage lies between the target sites.

Restriction endonucleases (restriction enzymes) are present in many species and are capable of sequence-specific binding to DNA (at a recognition site), and cleaving DNA at or near the site of binding. Certain restriction enzymes (e.g., Type IIS) cleave DNA at sites removed from the recognition site and have separable binding and cleavage domains. For example, the Type IIS enzyme Fok I catalyzes double-stranded cleavage of DNA, at 9 nucleotides from its recognition site on one strand and 13 nucleotides from its recognition site on the other. See, for example, U.S. Pat. Nos. 5,356,802; 5,436,150 and 5,487,994; as well as Li et al. (1992) *Proc. Natl. Acad. Sci. USA* 89:4275-4279; Li et al. (1993) *Proc. Natl. Acad. Sci. USA* 90:2764-2768; Kim et al. (1994a) *Proc. Natl. Acad. Sci. USA* 91:883-887; Kim et al. (1994b) *J. Biol. Chem.* 269:31,978-31,982. Thus, in one embodiment, fusion proteins comprise the cleavage domain (or cleavage half-domain) from at least one Type IIS restriction enzyme and one or more zinc finger binding domains, which may or may not be engineered.

An exemplary Type IIS restriction enzyme, whose cleavage domain is separable from the binding domain, is Fok I. This particular enzyme is active as a dimer. Bitinaite et al. (1998) *Proc. Natl. Acad. Sci. USA* 95: 10,570-10,575. Accordingly, for the purposes of the present disclosure, the portion of the Fok I enzyme used in the disclosed fusion proteins is considered a cleavage half-domain. Thus, for targeted double-stranded cleavage and/or targeted replacement of cellular sequences using zinc finger-Fok I fusions, two fusion proteins, each comprising a FokI cleavage half-domain, can be used to reconstitute a catalytically active cleavage domain. Alternatively, a single polypeptide molecule containing a zinc finger binding domain and two Fok I cleavage half-domains can also be used. Parameters for targeted cleavage and targeted sequence alteration using zinc finger-Fok I fusions are provided elsewhere in this disclosure.

A cleavage domain or cleavage half-domain can be any portion of a protein that retains cleavage activity, or that retains the ability to multimerize (e.g., dimerize) to form a functional cleavage domain.

Exemplary Type IIS restriction enzymes are described in International Publication WO 07/014275, incorporated herein in its entirety. Additional restriction enzymes also contain separable binding and cleavage domains, and these are contemplated by the present disclosure. See, for example, Roberts et al. (2003) *Nucleic Acids Res.* 31:418-420.

In certain embodiments, the cleavage domain comprises one or more engineered cleavage half-domain (also referred to as dimerization domain mutants) that minimize or prevent homodimerization, as described, for example, in U.S. Patent Publication Nos. 20050064474; 20060188987; 20090305346 and 20080131962, the disclosures of all of which are incorporated by reference in their entireties herein. Amino acid residues at positions 446, 447, 479, 483, 484, 486, 487, 490, 491, 496, 498, 499, 500, 531, 534, 537, and 538 of FokI are all targets for influencing dimerization of the FokI cleavage half-domains.

Exemplary engineered cleavage half-domains of FokI that form obligate heterodimers include a pair in which a first cleavage half-domain includes mutations at amino acid residues at positions 490 and 538 of FokI and a second cleavage half-domain includes mutations at amino acid residues 486 and 499.

Thus, in one embodiment, a mutation at 490 replaces Glu (E) with Lys (K); the mutation at 538 replaces Iso (I) with Lys (K); the mutation at 486 replaced Gln (Q) with Glu (E); and the mutation at position 499 replaces Iso (I) with Lys (K). Specifically, the engineered cleavage half-domains described herein were prepared by mutating positions 490 (E→K) and 538 (I→K) in one cleavage half-domain to produce an engineered cleavage half-domain designated "E490K:I538K" and by mutating positions 486 (Q→E) and 499 (I→L) in another cleavage half-domain to produce an engineered cleavage half-domain designated "Q486E:I499L". The engineered cleavage half-domains described herein are obligate heterodimer mutants in which aberrant cleavage is minimized or abolished. See, e.g., U.S. Pat. Nos. 7,914,796 and 8,034,598, the disclosures of which are incorporated by reference in their entireties for all purposes. In certain embodiments, the engineered cleavage half-domain comprises mutations at positions 486, 499 and 496 (numbered relative to wild-type FokI), for instance mutations that replace the wild type Gln (Q) residue at position 486 with a Glu (E) residue, the wild type Iso (I) residue at position 499 with a Leu (L) residue and the wild-type Asn (N) residue at position 496 with an Asp (D) or Glu (E) residue (also referred to as a "ELD" and "ELE" domains, respectively). In other embodiments, the engineered cleavage half-domain comprises mutations at positions 490, 538 and 537 (numbered relative to wild-type FokI), for instance mutations that replace the wild type Glu (E) residue at position 490 with a Lys (K) residue, the wild type Iso (I) residue at position 538 with a Lys (K) residue, and the wild-type His (H) residue at position 537 with a Lys (K) residue or a Arg (R) residue (also referred to as "KKK" and "KKR" domains, respectively). In other embodiments, the engineered cleavage half-domain comprises mutations at positions 490 and 537 (numbered relative to wild-type FokI), for instance mutations that replace the wild type Glu (E) residue at position 490 with a Lys (K) residue and the wild-type His (H) residue at position 537 with a Lys (K) residue or a Arg (R) residue (also referred to as "KIK" and "KIR" domains, respectively). (See U.S. Pat. No. 8,623,618). In other embodiments, the engineered cleavage half domain comprises the "Sharkey" and/or "Sharkey'" mutations (see Guo et al, (2010) *J. Mol. Biol.* 400(1):96-107).

Engineered cleavage half-domains described herein can be prepared using any suitable method, for example, by site-directed mutagenesis of wild-type cleavage half-domains (Fok I) as described in U.S. Pat. Nos. 7,888,121; 7,914,796; 8,034,598 and 8,623,618.

Alternatively, nucleases may be assembled in vivo at the nucleic acid target site using so-called "split-enzyme" technology (see, e.g. U.S. Patent Publication No. 20090068164). Components of such split enzymes may be expressed either on separate expression constructs, or can be linked in one open reading frame where the individual components are separated, for example, by a self-cleaving 2A peptide or IRES sequence. Components may be individual zinc finger binding domains or domains of a meganuclease nucleic acid binding domain.

Nucleases can be screened for activity prior to use, for example in a yeast-based chromosomal system as described in WO 2009/042163 and 20090068164. Nuclease expression constructs can be readily designed using methods known in the art. See, e.g., United States Patent Publications 20030232410; 20050208489; 20050026157; 20050064474; 20060188987; 20060063231; and International Publication WO 07/014275. Expression of the nuclease may be under the control of a constitutive promoter or an inducible promoter, for example the galactokinase promoter which is activated (de-repressed) in the presence of raffinose and/or galactose and repressed in presence of glucose.

In certain embodiments, the nuclease comprises a CRISPR/Cas system. The CRISPR (clustered regularly interspaced short palindromic repeats) locus, which encodes RNA components of the system, and the cas (CRISPR-associated) locus, which encodes proteins (Jansen et al., 2002. *Mol. Microbiol.* 43: 1565-1575; Makarova et al., 2002. *Nucleic Acids Res.* 30: 482-496; Makarova et al., 2006. *Biol. Direct* 1: 7; Haft et al., 2005. *PLoS Comput. Biol.* 1: e60) make up the gene sequences of the CRISPR/Cas nuclease system. CRISPR loci in microbial hosts contain a combination of CRISPR-associated (Cas) genes as well as non-coding RNA elements capable of programming the specificity of the CRISPR-mediated nucleic acid cleavage.

The Type II CRISPR is one of the most well characterized systems and carries out targeted DNA double-strand break in four sequential steps. First, two non-coding RNA, the pre-crRNA array and tracrRNA, are transcribed from the CRISPR locus. Second, tracrRNA hybridizes to the repeat regions of the pre-crRNA and mediates the processing of pre-crRNA into mature crRNAs containing individual spacer sequences. Third, the mature crRNA:tracrRNA complex directs Cas9 to the target DNA via Watson-Crick base-pairing between the spacer on the crRNA and the protospacer on the target DNA next to the protospacer adjacent motif (PAM), an additional requirement for target recognition. Finally, Cas9 mediates cleavage of target DNA to create a double-stranded break within the protospacer. Activity of the CRISPR/Cas system comprises of three steps: (i) insertion of alien DNA sequences into the CRISPR array to prevent future attacks, in a process called 'adaptation', (ii) expression of the relevant proteins, as well as expression and processing of the array, followed by (iii) RNA-mediated interference with the alien nucleic acid. Thus, in the bacterial cell, several of the so-called 'Cas' proteins are involved with the natural function of the CRISPR/Cas system and serve roles in functions such as insertion of the alien DNA etc.

In certain embodiments, Cas protein may be a "functional derivative" of a naturally occurring Cas protein. A "functional derivative" of a native sequence polypeptide is a compound having a qualitative biological property in common with a native sequence polypeptide. "Functional derivatives" include, but are not limited to, fragments of a native sequence and derivatives of a native sequence polypeptide and its fragments, provided that they have a biological activity in common with a corresponding native sequence polypeptide. A biological activity contemplated herein is the ability of the functional derivative to hydrolyze a DNA substrate into fragments. The term "derivative" encompasses both amino acid sequence variants of polypeptide, covalent modifications, and fusions thereof. Suitable derivatives of a Cas polypeptide or a fragment thereof include but are not limited to mutants, fusions, covalent modifications of Cas protein or a fragment thereof. Cas protein, which includes Cas protein or a fragment thereof, as well as derivatives of Cas protein or a fragment thereof, may be obtainable from a cell or synthesized chemically or by a combination of these two procedures. The cell may be a cell that naturally produces Cas protein, or a cell that naturally produces Cas protein and is genetically engineered to produce the endogenous Cas protein at a higher expression level or to produce a Cas protein from an exogenously introduced nucleic acid, which nucleic acid encodes a Cas that is same or different from the endogenous Cas. In some case, the cell does not naturally produce Cas protein and is genetically engineered to produce a Cas protein.

Exemplary CRISPR/Cas nuclease systems targeted to safe harbor and other genes are disclosed for example, in U.S. Publication No. 2015-0056705.

Thus, the nuclease comprises a DNA-binding domain that specifically binds to a target site in any gene into which it is desired to insert a donor (transgene).

Target Sites

As described in detail above, DNA-binding domains can be engineered to bind to any sequence of choice, for example in a safe-harbor locus such as albumin. An engineered DNA-binding domain can have a novel binding specificity, compared to a naturally-occurring DNA-binding domain. Engineering methods include, but are not limited to, rational design and various types of selection. Rational design includes, for example, using databases comprising triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, for example, co-owned U.S. Pat. Nos. 6,453,242 and 6,534,261, incorporated by reference herein in their entireties. Rational design of TAL-effector domains can also be performed. See, e.g., U.S. Pat. No. 8,586,526.

Exemplary selection methods applicable to DNA-binding domains, including phage display and two-hybrid systems, are disclosed in U.S. Pat. Nos. 5,789,538; 5,925,523; 6,007,988; 6,013,453; 6,410,248; 6,140,466; 6,200,759; and 6,242,568; as well as WO 98/37186; WO 98/53057; WO 00/27878; WO 01/88197 and GB 2,338,237. In addition, enhancement of binding specificity for zinc finger binding domains has been described, for example, in co-owned WO 02/077227.

Selection of target sites; nucleases and methods for design and construction of fusion proteins (and polynucleotides encoding same) are known to those of skill in the art and described in detail in U.S. Patent Application Publication Nos. 20050064474 and 20060188987, incorporated by reference in their entireties herein.

In addition, as disclosed in these and other references, DNA-binding domains (e.g., multi-fingered zinc finger proteins) may be linked together using any suitable linker sequences, including for example, linkers of 5 or more amino acids. See, e.g., U.S. Pat. Nos. 6,479,626; 6,903,185; and 7,153,949 for exemplary linker sequences 6 or more amino acids in length. The proteins described herein may include any combination of suitable linkers between the individual DNA-binding domains of the protein. See, also, U.S. Pat. No. 8,586,526.

DNA-binding domains of the nucleases may be targeted to any desired site in the genome. In certain embodiments, the DNA-binding domain of the nuclease is targeted to an endogenous safe harbor locus, for example an endogenous albumin locus.

Donor Sequences

Any donor can be inserted via nuclease-mediated targeted integration in the presence of a topoisomerase inhibitor as described herein. In certain embodiments, the donor comprises a polynucleotide (transgene) that encodes a therapeutic protein, for example a protein is lacking, deficient and/or aberrantly expressed in a subject with a disease or disorder. Non-limiting examples of such disorders include, epidermolysis bullosa, diabetes, cancer, clotting disorders or AAT deficient emphysema, clotting disorders and/or lysosomal storage diseases.

For treating hemophilia, the donor sequence (also called an "exogenous sequence" or "donor" or "transgene") comprises a sequence encoding a functional clotting factor protein, or part thereof, to result in a sequence encoding and expressing a functional clotting factor protein following donor integration. Non-limiting examples of clotting factor protein transgenes include Factor VIII and/or Factor IX, including functional fragments of these proteins. In certain embodiments, the B-domain of the F8 protein is deleted. See, e.g., Chuah et al. (2003) 101(5):1734-1743. In other embodiments, the transgene comprises a sequence encoding a functional F.IX protein, or part thereof, to result in a sequence encoding and expressing a function F.IX protein following donor integration. Similarly, for treating an LSD, the donor sequence encodes one or more proteins lacking in a subject with an LSD. Non-limiting examples of such proteins include glucocerebrosidase (GBA), which is deficient in Gaucher's; α galactosidase (GLA), which is deficient in Fabry's; iduronate-2-sulfatase deficiency (IDS), which is deficient in Hunter's; alpha-L iduronidase (IDUA), which is deficient in Hurler's; sphingomyelin phosphodiesterase 1 (SMPD1), which is deficient in Niemann-Pick's.

The donor molecule may be inserted into an endogenous gene such that all, some or none of the endogenous gene is expressed. For example, a transgene comprising functional clotting factor protein (e.g., F8 and/or F.IX) sequences as described herein may be inserted into an endogenous albumin locus such that some or none of the endogenous albumin is expressed with the transgene.

The cells can be exposed to the donor (transgene) sequence and topoisomerase inhibitors (and/or R-loop modifying and/or TC-NER-modifying compounds) as well as optional nucleases in any order, including concurrently (2 or more components) and/or sequentially in any order. In certain embodiments, the donor transgene is introduced into the cells before exposing the cells to the topoisomerase inhibitor(s), R-loop modifying and/or TC-NER-modifying compounds. In other embodiments, the donor transgene is introduced during and/or after exposing the cells to the topoisomerase inhibitor(s), R-loop modifying and/or TC-NER-modifying compounds.

The donor polynucleotide may contain sufficient homology (continuous or discontinuous regions) to a genomic sequence to support homologous recombination (or homology-directed repair) between it and the genomic sequence to which it bears homology or, alternatively, donor sequences can be integrated via non-HDR mechanisms (e.g., NHEJ donor capture), in which case the donor polynucleotide (e.g., vector) need not containing sequences that are homologous to the region of interest in cellular chromatin. See, e.g., U.S. Pat. Nos. 7,888,121 and 7,972,843 and U.S. Patent Publication No. 20110281361; 20100047805 and 20110207221.

The donor polynucleotide can be DNA or RNA, single-stranded, double-stranded or partially single- and partially double-stranded and can be introduced into a cell in linear or circular (e.g., minicircle) form. See, e.g., U.S. Patent Publication Nos. 20100047805, 20110281361, 20110207221. If introduced in linear form, the ends of the donor sequence can be protected (e.g., from exonucleolytic degradation) by methods known to those of skill in the art. For example, one or more dideoxynucleotide residues are added to the 3' terminus of a linear molecule and/or self-complementary oligonucleotides are ligated to one or both ends. See, for example, Chang et al. (1987) *Proc. Natl. Acad. Sci. USA* 84:4959-4963; Nehls et al. (1996) *Science* 272:886-889. Additional methods for protecting exogenous polynucleotides from degradation include, but are not limited to, addition of terminal amino group(s) and the use of modified internucleotide linkages such as, for example, phosphorothioates, phosphoramidates, and O-methyl ribose or deoxyribose residues. A polynucleotide can be introduced into a cell as part of a vector molecule having additional sequences such as, for example, replication origins, promoters and genes encoding antibiotic resistance. Moreover, donor polynucleotides can be introduced as naked nucleic acid, as nucleic acid complexed with an agent such as a liposome or poloxamer, or can be delivered by viruses (e.g., adenovirus, AAV, herpesvirus, retrovirus, lentivirus).

The donor is generally inserted so that its expression is driven by the endogenous promoter at the integration site (e.g., the endogenous albumin promoter when the donor is integrated into the patient's albumin locus). Thus, the transgene typically lacks control elements (e.g., promoter and/or enhancer) that drive its expression (e.g., also referred to as a "promoterless construct"). Nonetheless, it will be apparent that the donor may comprise a promoter and/or enhancer, for example a constitutive promoter or an inducible or tissue specific (e.g., liver- or platelet-specific) promoter that drives expression of the functional protein upon integration.

The donor sequence can be integrated specifically into any target site of choice, thereby eliminating the issues associated with random integration in traditional gene therapy.

When albumin sequences (endogenous or part of the transgene) are expressed with the transgene, the albumin sequences may be full-length sequences (wild-type or mutant) or partial sequences. Preferably the albumin sequences are functional. Non-limiting examples of the function of these full length or partial albumin sequences include increasing the serum half-life of the polypeptide expressed by the transgene (e.g., therapeutic gene) and/or acting as a carrier.

Furthermore, although not required for expression, exogenous sequences may also include transcriptional or translational regulatory sequences, for example, promoters, enhancers, insulators, internal ribosome entry sites, sequences encoding 2A peptides and/or polyadenylation signals.

Any of the donor sequences may include one or more of the following modifications: codon optimization (e.g., to human codons) and/or addition of one or more glycosylation sites. See, e.g., McIntosh et al. (2013) *Blood* (17):3335-44. Exogenous sequences may also comprise peptide sequences allowing for targeted delivery of a therapeutic protein. For example, nucleic acid sequences encoding the human p97 polypeptide and/or fragments thereof may be linked to a donor exogenous sequence such that the fusion protein will have the potential to cross the blood brain barrier (see e.g. U.S. Publication No. 20130183368 and Karkan et al (2008) *PLOS One*. DOI: 10.1371/journal.pone.0002469) or other peptides can be used to target a transgene donor encoded protein to intracellular organelles such as mitochondria (e.g. Jacotot et al (2006) *Biochim Biophys Acta Bioenerg* 1757: 1312-1323).

Delivery

The topoisomerase inhibitors, nucleases, polynucleotides encoding these nucleases, donor polynucleotides and compositions comprising the proteins and/or polynucleotides described herein may be delivered in vivo or ex vivo by any suitable means.

Delivery of topoisomerase inhibitors to cells (in vivo or ex vivo) is known in the art, including by direct delivery of small molecules use of liposomal formulations. See, e.g., U.S. Pat. No. 8,623,854. For delivery to cells, inhibitors can be delivered into the cell media. For in vivo delivery, topoisomerase inhibitors can be delivered via a variety of standard delivery mechanism, for example, orally, through intravenous injection, through intramuscular injection, subcutaneous injection and the like. For delivery of nucleic acid expression inhibitors to cause R-loop stabilization or inhibition of R-loop repair, nucleic acids (e.g. RNAi) can be delivered in vitro and in vivo via mechanisms known in the art, including by nanoparticles.

Methods of delivering nucleases as described herein are described, for example, in U.S. Pat. Nos. 8,586,526; 6,453,242; 6,503,717; 6,534,261; 6,599,692; 6,607,882; 6,689,558; 6,824,978; 6,933,113; 6,979,539; 7,013,219; and 7,163,824, the disclosures of all of which are incorporated by reference herein in their entireties.

Nucleases and/or donor constructs as described herein may also be delivered using vectors containing sequences encoding one or more of the zinc finger protein(s), TALEN protein(s) and/or a CRISPR/Cas system. Any vector systems may be used including, but not limited to, plasmid vectors, retroviral vectors, lentiviral vectors, adenovirus vectors, poxvirus vectors; herpesvirus vectors and adeno-associated virus vectors, etc. See, also, U.S. Pat. Nos. 6,534,261; 6,607,882; 6,824,978; 6,933,113; 6,979,539; 7,013,219; and 7,163,824, incorporated by reference herein in their entireties. Furthermore, it will be apparent that any of these vectors may comprise one or more of the sequences needed. Thus, when one or more nucleases and a donor construct are introduced into the cell, the nucleases and/or donor polynucleotide may be carried on the same vector or on different vectors. When multiple vectors are used, each vector may comprise a sequence encoding one or multiple nucleases and/or donor constructs. In certain embodiments, one vector is used to carry both the transgene and nuclease(s). In other embodiments, two vector are used (the same or different vector types), where one vector carries the nuclease(s) (e.g., left and right ZFNs of a ZFN pair, for example with a 2A peptide) and one carries the transgene. In still further embodiments, three vectors are used where the first vector carries one nuclease of a nuclease pair (e.g., left ZFN), the second vector carries the other nuclease of a nuclease pair (e.g., right ZFN) and the third vector carries the transgene.

The donors and/or nuclease may be used at any suitable concentrations. In certain embodiments, the donor and separate nuclease vector(s) are used the same concentration. In other embodiments, the donor and separate nuclease vector(s) are used at different concentrations, for example, 2-, 3-, 4-, 5-, 10- or more fold of one vector than other (e.g., more donor vector(s) than nuclease vector(s). When AAV vectors are used for delivery, for example, the donor- and/or nuclease-comprising viral vector(s) are between $1 \times 10^8$ and $1 \times 10^{13}$ particles per dose (e.g., cell or animal).

Conventional viral and non-viral based gene transfer methods can be used to introduce nucleic acids encoding nucleases and donor constructs in cells (e.g., mammalian cells) and target tissues. Non-viral vector delivery systems include DNA plasmids, naked nucleic acid, and nucleic acid complexed with a delivery vehicle such as a liposome or poloxamer. Viral vector delivery systems include DNA and RNA viruses, which have either episomal or integrated genomes after delivery to the cell. For a review of in vivo delivery of engineered DNA-binding proteins and fusion proteins comprising these binding proteins, see, e.g., Rebar (2004) *Expert Opinion Invest. Drugs* 13(7):829-839; Rossi et al. (2007) *Nature Biotech.* 25(12):1444-1454 as well as general gene delivery references such as Anderson, *Science* 256:808-813 (1992); Nabel & Felgner, *TIBTECH* 11:211-217 (1993); Mitani & Caskey, *TIBTECH* 11:162-166 (1993); Dillon, *TIBTECH* 11:167-175 (1993); Miller, *Nature* 357: 455-460 (1992); Van Brunt, *Biotechnology* 6(10):1149-1154 (1988); Vigne, *Restorative Neurology and Neuroscience* 8:35-36 (1995); Kremer & Perricaudet, *British Medical Bulletin* 51(1):31-44 (1995); Haddada et al., in *Current Topics in Microbiology and Immunology* Doerfler and Böhm (eds.) (1995); and Yu et al., *Gene Therapy* 1:13-26 (1994).

Methods of non-viral delivery of nucleic acids include electroporation, lipofection, microinjection, biolistics, virosomes, liposomes, immunoliposomes, polycation or lipid: nucleic acid conjugates, naked DNA, artificial virions, and agent-enhanced uptake of DNA. Sonoporation using, e.g., the Sonitron 2000 system (Rich-Mar) can also be used for delivery of nucleic acids.

Additional exemplary nucleic acid delivery systems include those provided by AmaxaBiosystems (Cologne, Germany), Maxcyte, Inc. (Rockville, Md.), BTX Molecular Delivery Systems (Holliston, Mass.) and Copernicus Therapeutics Inc, (see for example U.S. Pat. No. 6,008,336). Lipofection is described in e.g., U.S. Pat. Nos. 5,049,386; 4,946,787; and 4,897,355) and lipofection reagents are sold commercially (e.g., Transfectam™ and Lipofectin™). Cationic and neutral lipids that are suitable for efficient receptor-recognition lipofection of polynucleotides include those of Felgner, WO 91/17424, WO 91/16024.

The preparation of lipid:nucleic acid complexes, including targeted liposomes such as immunolipid complexes, is well known to one of skill in the art (see, e.g., Crystal, *Science* 270:404-410 (1995); Blaese et al., *Cancer Gene Ther.* 2:291-297 (1995); Behr et al., *Bioconjugate Chem.* 5:382-389 (1994); Remy et al., *Bioconjugate Chem.* 5:647-654 (1994); Gao et al., *Gene Therapy* 2:710-722 (1995); Ahmad et al., *Cancer Res.* 52:4817-4820 (1992); U.S. Pat. Nos. 4,186,183, 4,217,344, 4,235,871, 4,261,975, 4,485,054, 4,501,728, 4,774,085, 4,837,028, and 4,946,787).

Additional methods of delivery include the use of packaging the nucleic acids to be delivered into EnGeneIC delivery vehicles (EDVs). These EDVs are specifically delivered to target tissues using bispecific antibodies where one arm of the antibody has specificity for the target tissue and the other has specificity for the EDV. The antibody brings the EDVs to the target cell surface and then the EDV is brought into the cell by endocytosis. Once in the cell, the contents are released (see MacDiarmid et al (2009) *Nature Biotechnology* 27(7):643).

The use of RNA or DNA viral based systems for the delivery of nucleic acids encoding engineered nucleases and/or donors take advantage of highly evolved processes for targeting a virus to specific cells in the body and trafficking the viral payload to the nucleus. Viral vectors can be administered directly to patients (in vivo) or they can be used to treat cells in vitro and the modified cells are administered to patients (ex vivo). Conventional viral based systems for the delivery of nucleases and/or donors include, but are not limited to, retroviral, lentivirus, adenoviral, adeno-associated, vaccinia and herpes simplex virus vectors for gene transfer. Integration in the host genome is possible with the retrovirus, lentivirus, and adeno-associated virus gene transfer methods, often resulting in long term expression of the inserted transgene. Additionally, high transduction efficiencies have been observed in many different cell types and target tissues.

The tropism of a retrovirus can be altered by incorporating foreign envelope proteins, expanding the potential target population of target cells. Lentiviral vectors are retroviral vectors that are able to transduce or infect non-dividing cells and typically produce high viral titers. Selection of a retroviral gene transfer system depends on the target tissue. Retroviral vectors are comprised of cis-acting long terminal repeats with packaging capacity for up to 6-10 kb of foreign sequence. The minimum cis-acting LTRs are sufficient for replication and packaging of the vectors, which are then used to integrate the therapeutic gene into the target cell to provide permanent transgene expression. Widely used retroviral vectors include those based upon murine leukemia virus (MuLV), gibbon ape leukemia virus (GaLV), Simian Immunodeficiency virus (SIV), human immunodeficiency virus (HIV), and combinations thereof (see, e.g., Buchscher et al., *J. Virol.* 66:2731-2739 (1992); Johann et al., *J. Virol.* 66:1635-1640 (1992); Sommerfelt et al., *Virol.* 176:58-59 (1990); Wilson et al., *J. Virol.* 63:2374-2378 (1989); Miller et al., *J. Virol.* 65:2220-2224 (1991); PCT/US94/05700).

In applications in which transient expression is preferred, adenoviral based systems can be used. Adenoviral based vectors are capable of very high transduction efficiency in many cell types and do not require cell division. With such vectors, high titer and high levels of expression have been obtained. This vector can be produced in large quantities in a relatively simple system. Adeno-associated virus ("AAV") vectors are also used to transduce cells with target nucleic acids, e.g., in the in vitro production of nucleic acids and peptides, and for in vivo and ex vivo gene therapy procedures (see, e.g., West et al., *Virology* 160:38-47 (1987); U.S. Pat. No. 4,797,368; WO 93/24641; Kotin, *Human Gene Therapy* 5:793-801 (1994); Muzyczka, *J. Clin. Invest.* 94:1351 (1994). Construction of recombinant AAV vectors is described in a number of publications, including U.S. Pat. No. 5,173,414; Tratschin et al., *Mol. Cell. Biol.* 5:3251-3260 (1985); Tratschin, et al., *Mol. Cell. Biol.* 4:2072-2081 (1984); Hermonat & Muzyczka, *PNAS* 81:6466-6470 (1984); and Samulski et al., *J. Virol.* 63:03822-3828 (1989).

At least six viral vector approaches are currently available for gene transfer in clinical trials, which utilize approaches that involve complementation of defective vectors by genes inserted into helper cell lines to generate the transducing agent.

pLASN and MFG-S are examples of retroviral vectors that have been used in clinical trials (Dunbar et al., *Blood* 85:3048-305 (1995); Kohn et al., *Nat. Med.* 1:1017-102 (1995); Malech et al., *PNAS* 94:22 12133-12138 (1997)). PA317/pLASN was the first therapeutic vector used in a gene therapy trial. (Blaese et al., *Science* 270:475-480 (1995)). Transduction efficiencies of 50% or greater have been observed for MFG-S packaged vectors. (Ellem et al., *Immunol Immunother* 44(1):10-20 (1997); Dranoff et al., *Hum. Gene Ther.* 1:111-2 (1997).

Recombinant adeno-associated virus vectors (rAAV) are a promising alternative gene delivery systems based on the defective and nonpathogenic parvovirus adeno-associated type 2 virus. All vectors are derived from a plasmid that retains only the AAV 145 base pair inverted terminal repeats flanking the transgene expression cassette. Efficient gene transfer and stable transgene delivery due to integration into the genomes of the transduced cell are key features for this vector system. (Wagner et al., *Lancet* 351:9117 1702-3 (1998), Kearns et al., *Gene Ther.* 9:748-55 (1996)). Other AAV serotypes, including AAV1, AAV3, AAV4, AAV5, AAV6, AAV8, AAV9 and AAVrh10 or pseudotyped AAV such as AAV2/8, AAV8.2, AAV2/5 and AAV2/6 and any novel AAV serotype can also be used in accordance with the present invention.

Replication-deficient recombinant adenoviral vectors (Ad) can be produced at high titer and readily infect a number of different cell types. Most adenovirus vectors are engineered such that a transgene replaces the Ad E1a, E1b, and/or E3 genes; subsequently the replication defective vector is propagated in human 293 cells that supply deleted gene function in trans. Ad vectors can transduce multiple types of tissues in vivo, including nondividing, differentiated cells such as those found in liver, kidney and muscle. Conventional Ad vectors have a large carrying capacity. An example of the use of an Ad vector in a clinical trial involved polynucleotide therapy for antitumor immunization with intramuscular injection (Sterman et al., *Hum. Gene Ther.* 7:1083-9 (1998)). Additional examples of the use of adenovirus vectors for gene transfer in clinical trials include Rosenecker et al., *Infection* 24:1 5-10 (1996); Sterman et al., *Hum. Gene Ther.* 9:7 1083-1089 (1998); Welsh et al., *Hum. Gene Ther.* 2:205-18 (1995); Alvarez et al., *Hum. Gene Ther.* 5:597-613 (1997); Topf et al., *Gene Ther.* 5:507-513 (1998); Sterman et al., *Hum. Gene Ther.* 7:1083-1089 (1998).

Packaging cells are used to form virus particles that are capable of infecting a host cell. Such cells include 293 cells, which package adenovirus, and ψ2 cells or PA317 cells, which package retrovirus. Viral vectors used in gene therapy are usually generated by a producer cell line that packages a nucleic acid vector into a viral particle. The vectors typically contain the minimal viral sequences required for packaging and subsequent integration into a host (if applicable), other viral sequences being replaced by an expression cassette encoding the protein to be expressed. The missing viral functions are supplied in trans by the packaging cell line. For example, AAV vectors used in gene therapy typically only possess inverted terminal repeat (ITR) sequences from the AAV genome which are required for packaging and integration into the host genome. Viral DNA is packaged in a cell line, which contains a helper plasmid encoding the other AAV genes, namely rep and cap, but lacking ITR sequences. The cell line is also infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV.

In many gene therapy applications, it is desirable that the gene therapy vector be delivered with a high degree of specificity to a particular tissue type. Accordingly, a viral vector can be modified to have specificity for a given cell type by expressing a ligand as a fusion protein with a viral coat protein on the outer surface of the virus. The ligand is chosen to have affinity for a receptor known to be present on the cell type of interest. For example, Han et al., *Proc. Natl. Acad. Sci. USA* 92:9747-9751 (1995), reported that Moloney murine leukemia virus can be modified to express human heregulin fused to gp70, and the recombinant virus infects certain human breast cancer cells expressing human epidermal growth factor receptor. This principle can be extended to other virus-target cell pairs, in which the target cell expresses a receptor and the virus expresses a fusion protein comprising a ligand for the cell-surface receptor. For example, filamentous phage can be engineered to display antibody fragments (e.g., FAB or Fv) having specific binding affinity for virtually any chosen cellular receptor. Although the above description applies primarily to viral vectors, the same principles can be applied to nonviral vectors. Such vectors can be engineered to contain specific uptake sequences which favor uptake by specific target cells.

Gene therapy vectors can be delivered in vivo by administration to an individual patient, typically by systemic administration (e.g., intravenous, intraperitoneal, intramuscular, subdermal, or intracranial infusion) or topical application, as described below. Alternatively, vectors can be delivered to cells ex vivo, such as cells explanted from an individual patient (e.g., lymphocytes, bone marrow aspirates, tissue biopsy) or universal donor hematopoietic stem cells, followed by reimplantation of the cells into a patient, usually after selection for cells which have incorporated the vector.

Vectors (e.g., retroviruses, adenoviruses, liposomes, etc.) containing nucleases and/or donor constructs can also be administered directly to an organism for transduction of cells in vivo. Alternatively, naked DNA can be administered. Administration is by any of the routes normally used for introducing a molecule into ultimate contact with blood or tissue cells including, but not limited to, injection, infusion, topical application and electroporation. Suitable methods of administering such nucleic acids are available and well known to those of skill in the art, and, although more than one route can be used to administer a particular composition, a particular route can often provide a more immediate and more effective reaction than another route.

Vectors suitable for introduction of polynucleotides (e.g. nuclease-encoding and/or donors) described herein include non-integrating lentivirus vectors (IDLV). See, for example, Ory et al. (1996) *Proc. Natl. Acad. Sci. USA* 93:11382-11388; Dull et al. (1998) *J. Virol.* 72:8463-8471; Zuffery et al. (1998) *J. Virol.* 72:9873-9880; Follenzi et al. (2000) *Nature Genetics* 25:217-222; U.S. Pat. No. 8,936,936.

Pharmaceutically acceptable carriers are determined in part by the particular composition being administered, as well as by the particular method used to administer the composition. Accordingly, there is a wide variety of suitable formulations of pharmaceutical compositions available, as described below (see, e.g., *Remington's Pharmaceutical Sciences,* 17th ed., 1989).

Delivery in vitro and in vivo may also be accomplished through the use of nanoparticles. Many nanoparticles currently being investigated are comprised of therapeutic molecules that self-assemble with lipids or polymers into nanostructures. These particles have the potential to deliver therapeutic doses of nucleic acids to target tissues (e.g. tumor cells, specific organs etc.). See e.g. Rink et al (2013), *Curr Opin Oncol:* 25(6): p. 646-651.

It will be apparent that the nuclease-encoding sequences and donor constructs can be delivered using the same or different systems. For example, the nucleases and donors can be carried by the same vector (e.g., AAV). Alternatively, a donor polynucleotide can be carried by a plasmid, while the one or more nucleases can be carried by a different vector (e.g., AAV vector). Furthermore, the different vectors can be administered by the same or different routes (intramuscular injection, tail vein injection, other intravenous injection, intraperitoneal administration and/or intramuscular injection. The vectors can be delivered simultaneously or in any sequential order.

Thus, the instant disclosure includes in vivo or ex vivo treatment and/or prevention of a disease or disorder in which a protein is lacking or deficient. For instance, Hemophilia A may be treated, via nuclease-mediated integration of F8-encoding sequence. The disclosure also includes in vivo or ex vivo treatment of Hemophilia B, via nuclease-mediated integration of a F.IX encoding sequence. Similarly, the disclosure includes the treatment of Factor VII deficiency and Factor X deficiency related hemophilias via nuclease-mediated integration of a Factor VII or Factor X encoding sequence, respectively. In addition, the disclosure includes the treatment of one or more LSDs via nuclease-mediated integration of one or more proteins lacking or deficient in the LSD. The compositions are administered to a human patient in an amount effective to obtain the desired concentration of the therapeutic polypeptide in the serum, the liver or the target cells. Administration can be by any means in which the polynucleotides are delivered to the desired target cells. For example, both in vivo and ex vivo methods are contemplated. Intravenous injection to the portal vein is a preferred method of administration. Other in vivo administration modes include, for example, direct injection into the lobes of the liver or the biliary duct and intravenous injection distal to the liver, including through the hepatic artery, direct injection in to the liver parenchyma, injection via the hepatic artery, and/or retrograde injection through the biliary tree. See, e.g., U.S. Patent Publication No. 20140017212 regarding in vivo delivery of transgenes (and/or nucleases) to the liver. Ex vivo modes of administration include transduction in vitro of resected hepatocytes or other cells of the liver, followed by infusion of the transduced, resected hepatocytes back into the portal vasculature, liver parenchyma or biliary tree of the human patient, see e.g., Grossman et al. (1994) *Nature Genetics,* 6:335-341. Other modes of administration include the ex vivo nuclease-mediated insertion of a Factor VII, F8, F.IX, Factor X, glucocerebrosidase, α galactosidase, iduronate-2-sulfatase, and/or alpha-L iduronidase encoding transgene into a safe harbor location into patient or allogenic stem cells. Following modification, the treated cells are then re-infused into the patient for treatment of the disease or disorder (e.g., LSD and/or a hemophilia).

The effective amount of nuclease(s) and donor (e.g., Factor VII, F8, F.IX, Factor X, GBA, GLA, IDS, IDUA, or SMPD1) to be administered will vary from patient to patient and according to the therapeutic polypeptide of interest. Accordingly, effective amounts are best determined by the physician administering the compositions and appropriate dosages can be determined readily by one of ordinary skill in the art. After allowing sufficient time for integration and expression (typically 4-15 days, for example), analysis of the serum or other tissue levels of the therapeutic polypeptide and comparison to the initial level prior to administration will determine whether the amount being administered is too low, within the right range or too high. Suitable regimes for initial and subsequent administrations are also variable, but are typified by an initial administration followed by subsequent administrations if necessary. Subsequent administrations may be administered at variable intervals, ranging from daily to annually to every several years. One of skill in the art will appreciate that appropriate immunosuppressive techniques may be recommended to avoid inhibition or blockage of transduction by immunosuppression of the delivery vectors, see e.g., Vilquin et al. (1995) *Human Gene Ther.* 6:1391-1401.

Formulations for both ex vivo and in vivo administrations include suspensions in liquid or emulsified liquids. The active ingredients often are mixed with excipients which are pharmaceutically acceptable and compatible with the active ingredient. Suitable excipients include, for example, water, saline, dextrose, glycerol, ethanol or the like, and combinations thereof. In addition, the composition may contain minor amounts of auxiliary substances, such as, wetting or emulsifying agents, pH buffering agents, stabilizing agents or other reagents that enhance the effectiveness of the pharmaceutical composition.

Applications

The methods and compositions of the invention can be used in any circumstance wherein it is desired to increase gene targeted rates of donor sequences to supply one or more transgenes encoding one or more proteins such that the protein(s) is(are) produced by the target cell (including where the protein(s) is(are) secreted from the targeted cell). Thus, this technology is of use in a condition where a patient is deficient in some protein due to problems (e.g., problems in expression level or problems with the protein expressed as sub- or non-functioning). Additionally, A1AT-deficiency disorders such as COPD or liver damage, or other disorders, conditions or diseases that can be mitigated by the supply of exogenous proteins by a secretory organ may be successfully treated by the methods and compositions of this invention. Lysosomal storage diseases can be treated by the methods and compositions of the invention, as are metabolic diseases such as diabetes.

Proteins that are useful therapeutically and that are typically delivered by injection or infusion are also useful with the methods and compositions of the invention. By way of non-limiting examples, production of a C-peptide (e.g. Ersatta™ by Cebix) or insulin for use in diabetic therapy. A further application includes treatment of Epidermolysis Bullosa via production of collagen VII. Expression of IGF-1 in secretory tissue as described herein can be used to increase levels of this protein in patients with liver cirrhosis and lipoprotein lipase deficiency by expression of lipoprotein lipase. Antibodies may also be secreted for therapeutic benefit, for example, for the treatment of cancers, autoimmune and other diseases. Examples of therapeutic antibodies include antibodies against TNF-α, EpCAM, CD20, CD19, VEGFR, CD52 and the like. Other proteins related to clotting could be produced in secretory tissue, include fibrinogen, prothrombin, tissue factor, Factor V, Factor XI, Factor XII (Hageman factor), Factor XIII (fibrin-stabilizing factor), von Willebrand factor, prekallikrein, high molecular weight kininogen (Fitzgerald factor), fibronectin, antithrombin III, heparin cofactor II, protein C, protein S, protein Z, protein Z-related protease inhibitor, plasminogen, alpha 2-antiplasmin, tissue plasminogen activator, urokinase, plasminogen activator inhibitor-1, and plasminogen activator inhibitor-2.

The methods and compositions of the invention involving the use of topoisomerase inhibitors can also be used in any circumstance wherein it is desired to enhance targeted integration of a transgene encoding one or more non-coding or structural nucleic acids (e.g. shRNA or RNAi). Such RNAs may form inhibitory structures and be useful in the treatment of diseases such as lipid disorders (targeting e.g. ApoB-100, ApoC-III, ANGPTL3, PCSK9); coronary artery disease (targeting e.g. CRP, Apo(a)); clotting and blood disorders (targeting e.g. F.XI, FVII, antithrombin, TMPRSS6); autoimmune diseases (targeting e.g. ICAM-1, GCCR, GCGR, PTP-1B, VLA-4); TTR amyloidosis; muscular diseases (targeting e.g. SMN2, GHr, DMPK); inflammatory disease (targeting e.g. PKK); obesity (targeting e.g. FGFR4); liver disease (targeting e.g. DGAT2, ALAS-1, C5, AAT); Cancer (targeting e.g. clusterin, eIF-4E, Hsp27, AR); fibrotic disease (targeting e.g. CTGF); ocular disease (targeting e.g. C-raf kinase); or infectious disease (targeting e.g. aminoglycodise, hepcidin, RG-101).

The following Examples relate to exemplary embodiments of the present disclosure in which the nuclease comprises a zinc finger nuclease (ZFN) or TALEN. It will be appreciated that this is for purposes of exemplification only and that other nucleases can be used or that targeted integration can be performed in the absence of nucleases, for instance homing endonucleases (meganucleases) with engineered DNA-binding domains and/or fusions of naturally occurring of engineered homing endonucleases (meganucleases) DNA-binding domains and heterologous cleavage domains, and/or a CRISPR/Cas system comprising an engineered single guide RNA.

EXAMPLES

Example 1

Increasing Targeted Integration Using Topoisomerase Inhibitors

Isolated cells (e.g., hepatic or CD34+ cells) or HA/CD4−/− mice are administered either (1) donors transgenes (e.g., in plasmid, mRNA or viral vector form); (2) nucleases (ZFNs TALENs and/or CRISPR/Cas nucleases) targeting the albumin locus (as described in U.S. Patent Publication 20130177983; 20150159172 and 2015-0056705) (e.g., in plasmid, mRNA or viral vector form) and/or; (3) one or more topoisomerase inhibitors, one or more stabilizers of R loop formation; one or more inhibitors of R-loop repair; and/or one or more up-regulators of the TC-NER pathway. Mice are administered by the components by injection to the tail vein as described in U.S. Patent Publication No. 20120128635. Exemplary donors encode proteins lacking or deficient in Lysosomal Storage Disease such as IDS or IDUA, proteins lacking in hemophilias (e.g., Factors VII, VIII and/or IX) and optionally include homology arms flanking the transgene.

Topoisomerase inhibitors, R-loop stabilizers, inhibitors of R-loop repair and TC-NER up-regulators increase gene targeted frequency of the donor in the presence of the nucleases as compared to control cells in which the compounds were not administered.

For instance, one-hundred thousand Hepa1-6 cells were seeded per well of a 24-well dish and grown until 70% confluent in DMEM+10% FBS. Cells were either left untreated, treated with DMSO alone, treated with 0.5-5 uM etoposide (dissolved in DMSO) or treated with 0.5-5 uM camptothecin (dissolved in DMSO) where treatment involved adding the compound to the culture media. Cells were then transfected with one of two Factor IX (FIX)-containing adeno-associated viruses (AAVs) donors (e.g., AAV2/6 vectors at 6e10 vg per sample) and Factor IX production on days 0-4 (day 4) and days 5-7 (day 7) assayed by ELISA.

The FIX donor AAVs contain homology arms (complementary to the 3' end of the mouse albumin gene) flanking an albumin 3' intron splice acceptor-albumin 3' exon-2A-Factor IX cassette. In one instance, the Factor IX cassette was positioned in the forward orientation (F), allowing Factor IX to be produced if the DNA was integrated into the Albumin locus through HDR by the use of the homology arms. In the other instance, the Factor IX cassette was in the reverse orientation (R), and did not permit Factor IX expression after integration into the albumin gene if integrated via NHEJ-mediated end capture.

Topoisomerase inhibition causes DNA damage not only at the albumin gene but throughout the genome as well. This DNA damage allows the intended, homology-driven integration of FIX at the albumin locus and also allows some amount of off-target integration of both forward- and reverse-orientation FIX-AAV genomes via non-homologous end joining. If captured within a transcribed gene, and if captured in the same orientation as that gene, these off-target integration events result in the expression of Factor IX. Therefore, we determined the stimulation of Factor IX integration/expression that is specific to integration at the albumin gene in the proper orientation; this number is roughly equal to the Factor IX produced from the forward-orientation virus minus the Factor IX produced by the reverse-orientation virus.

As shown in FIG. 1, there was a marked (>55× at the highest doses) stimulation of Factor IX production in the presence of the topoisomerase inhibitor, and this increase expression was largely associated to the forward-orientation virus.

Example 2

Engraftment of Engineered CD34+ Cells into NSG Mice

Human CD34+ HSC that are nucleofected with a transgene donor as described above are used to engraft NSG mice to make "humanized mice" using standard protocols, for example as described in Holt et al. (2010), Nature Biotech. 28:839-47. Samples are taken from the peripheral blood of the mice by standard methodology at 4, 8, 12, 16, and 20 weeks post engraftment, also as described in Holt et al. ibid.

The ability of the cells to successfully engraft the mice and produce human CD45+ progeny blood cells is analyzed by evaluating the expression of human CD45 on leucocytes by FACs analysis, also described in Holt et al. ibid. The experiments show that cells that are transformed with the transgenes show engraftment. Additionally, at 20 weeks, the animals are sacrificed and an analysis is done to determine the percent of human CD45 positive cells in the blood, bone marrow and spleen by FACs analysis as described above.

The results show that the cells that are nucleofected with the transgene are able to establish themselves in the NSG mouse tissues such as bone marrow and spleen.

All patents, patent applications and publications mentioned herein are hereby incorporated by reference in their entirety.

Although disclosure has been provided in some detail by way of illustration and example for the purposes of clarity of understanding, it will be apparent to those skilled in the art that various changes and modifications can be practiced without departing from the spirit or scope of the disclosure. Accordingly, the foregoing descriptions and examples should not be construed as limiting.

What is claimed is:

1. A method of integrating a transgene encoding a protein in a forward orientation into a selected endogenous genomic locus of an isolated population of liver or hematopoietic stem cells, the method comprising:
   treating the isolated liver or hematopoietic stem cells with at least one topoisomerase inhibitor, the at least one topoisomerase inhibitor comprising camptothecin or etoposide;
   introducing an AAV vector into the treated population of isolated liver or hematopoietic stem cells, the AAV vector comprising regions of homology to the selected endogenous genomic locus flanking the transgene, wherein the population of liver or hematopoietic stem cells is grown in the presence of the at least one topoisomerase inhibitor, such that the transgene is integrated into the selected endogenous locus in a forward orientation and expression of the transgene is driven an endogenous promoter and further wherein the transgene is integrated into the selected endogenous genomic locus and the protein is expressed from the endogenous promoter at levels increased at least 5-fold as compared to cells not grown in the presence of the at least one topoisomerase inhibitor.

2. The method of claim 1, wherein the topoisomerase inhibitor inhibits topoisomerase I and/or II.

3. The method of claim 2, further comprising treating the isolated liver or hematopoietic stem cells with doxorubicin, cisplatin, topotecan, irinotecan, tenipopside, mitoxantrone, etoposide phosphate, and/or topotecan hydrochloride.

4. The method of claim 1, further comprising introducing one or more nucleases targeted to the selected endogenous genomic locus.

5. The method of claim 4 wherein the selected endogenous locus is an endogenous safe-harbor gene.

6. The method of claim 5, wherein the safe harbor gene is selected from the group consisting of a CCR5 gene, an HPRT gene, an AAVS1 gene, a Rosa gene or an albumin gene.

7. The method of claim 6, wherein the safe harbor gene is an albumin gene.

8. The method of claim 7, wherein expression of the transgene is controlled by an endogenous albumin promoter.

9. The method of claim 4, wherein the one or more nucleases comprise a zinc finger nuclease (ZFN), a TALEN or CRISPR/Cas nuclease system.

10. The method of claim 1, wherein the protein is deficient or lacking in a subject with a lysosomal storage disease, hemophilia, epidermolysis bullosa, diabetes, cancer, clotting disorders or AAT deficient emphysema.

11. The method of claim 1, wherein the protein is a Factor VII protein, a Factor VIII (F8) protein, a Factor IX (F.IX) protein, a Factor X protein, a glucocerebrosidase protein, an α galactosidase protein, an iduronate-2-sulfatase protein, an alpha-L iduronidase protein and/or a sphingomyelin phosphodiesterase protein.

* * * * *